United States Patent [19]

Radhakrishnan

[11] Patent Number: 5,043,165

[45] Date of Patent: * Aug. 27, 1991

[54] NOVEL LIPOSOME COMPOSITION FOR SUSTAINED RELEASE OF STEROIDAL DRUGS

[75] Inventor: Ramachandran Radhakrishnan, Fremont, Calif.

[73] Assignee: Liposome Technology, Inc., Menlo Park, Calif.

[*] Notice: The portion of the term of this patent subsequent to Mar. 6, 2007 has been disclaimed.

[21] Appl. No.: 284,216

[22] Filed: Dec. 14, 1988

[51] Int. Cl.$^5$ .............................................. A61K 37/22
[52] U.S. Cl. .................................... 424/450; 424/1.1; 424/9; 514/180
[58] Field of Search ........................... 424/450, 9, 1.1; 514/180

[56] References Cited

U.S. PATENT DOCUMENTS

| | | | |
|---|---|---|---|
| 4,224,179 | 9/1980 | Schneider | 424/450 |
| 4,235,871 | 11/1980 | Parahadjopoulos et al. | 424/450 |
| 4,515,736 | 5/1985 | Deamer | 424/9 |
| 4,693,999 | 9/1987 | Axelsson et al. | 514/180 |
| 4,746,516 | 5/1988 | Moro et al. | 514/36 |
| 4,780,455 | 10/1988 | Lieberman et al. | 514/182 |

Primary Examiner—Thurman K. Page
Assistant Examiner—P. L. Prater
Attorney, Agent, or Firm—Hana Dolezalova

[57] ABSTRACT

This invention relates to a novel, non-conventional liposome formulation for the sustained release and delivery of steroids. The formulation provides prolonged release of the drug, improved therapeutic ratio, lower toxicity, reduced systemic side effects and is stable for up to three months. The formulation is suitable for sustained delivery of steroid via inhalation, parenteral, intrathecal, intraarticular, topical, ophthalmic, and oral administration.

43 Claims, 7 Drawing Sheets

NOVEL LIPOSOME COMPOSITION FOR SUSTAINED RELEASE OF STEROIDAL DRUGS

BACKGROUND OF THE INVENTION

1. Field of the Invention

The present invention relates to a novel nonconventional liposome composition enabling an efficient loading and sustained release of steroidal drugs. The composition is particularly useful in formulating steroids for inhalation, targeted systemic, parenteral, oral, intrathecal, intraarticular, nasal, ophthalmic and topical administrations for human and veterinary therapeutic applications.

2. Related Disclosures

Steroids, in particular corticosteroids, have been found to have a wide repertoire of therapeutic applications. For pharmaceutical use, these steroids are synthesized as structural analogues of the adrenocortical hormone hydrocortisone. Corticosteroids have powerful effects on immunologic and hormonal processes, and are very effective in treating a wide range of inflammatory diseases, such as arthritis, rheumatoid arthritis, allergic reactions and conditions such as asthma, pulmonary fibrosis and other lung diseases, and are widely used for treatment of ophthalmic and dermatological irritations.

As with many potent drugs given systemically, the therapeutic benefits of corticosteroids are accompanied by an array of deleterious side effects, such as, among others, muscular atrophy, disruption of adrenal-pituitary axis resulting in stunted growth in children, edema, hypertension, osteoporosis, glaucoma, damage to the immune system leading to susceptibility to viral and fungal infections, psychological disorders, and even heart failure.

Attempts to minimize these complications were not very successful. For example, daily systemic administration of smaller, insufficient and inadequate doses of steroids for desired therapy led to unsuccessful or prolonged treatments. On the other hand, an administration of the higher doses of steroids on alternate days led to uneven levels and peaks in the blood level of the steroid. High level peaks of steroid were followed by the side effects. Both, extended treatment and side effects, were found to be highly undesirable.

Thus, it would be greatly advantageous to provide a pharmaceutical formulation which would allow slow but sustained release of steroids preferably only at the target organ.

Some improvements were achieved by focusing on administration of steroids via routes that diminish the systemic side effects elsewhere in the body, or by formulating them in delivery systems that might improve the benefit-to-toxicity therapeutic ratio. However, because of steroids' poor solubility in water, these attempts to formulate steroids in an appropriate vehicles for particular therapies have been, in general, unsuccessful.

Thus, it would be advantageous to have available a steroid composition formulated in such a way as to carry to and release in the particular organ in need of such therapy an effective dose for extended periods of time using the minimum amount of steroid. By solving such formulation challenges, that is, by developing an appropriate formulation vehicle for each therapy, the undesirable side effects accompanying steroid therapies would be diminished.

Some of the difficulties connected with steroid formulation are due to the fact that steroids are poorly soluble or insoluble in water. For that reason, methods previously used to obtain effective formulation have relied either on use of organic solvents or on crystalline suspensions in an aqueous medium. Organic solvents such as ethanol, butanol, propanol and others are prone to cause tissue irritation and may be painful when administered by certain routes.

To avoid the severe systemic side effects, one of the commonly used preferred route of administration of steroids for treatment of pulmonary conditions is via inhalation. However, the inhalation of normally formulated steroids leads to a rapid absorption, introducing the possibility of overdose or necessitating the more frequent dosing when lower doses are used, which in turn, cause the heightening of systemic side effects. Notwithstanding, even the normally formulated steroidal inhalants are preferable for replacing systemically-administered steroids because they reduce, albeit not eliminate, the side effects when inhaled at recommended doses. The need for repeated dosing however remains. That need can only be avoided by providing the formulation allowing for sustained controlled release of the steroid.

The advantage of inhalation administration of steroids over the systemic administration can best be illustrated using, for example, a potent antiinflammatory steroid dexamethasone. Dexamethasone is normally administered systemically by i.v. injection in doses ranging from 0.5 to 9 mg/day with even higher doses required in certain severe conditions. Where, however, dexamethasone is administered via inhalation, the dose is approximately 0.084 mg. The total dose of inhaled dexamethasone daily, even when the inhalation is repeated at the maximum dosing frequency, i.e. 12 times a day, corresponds to 0.4 to 0.6 mg to a maximum of around 1.0 mg of absorbed dexamethasone a day. PDR: 1312 and 1315 (1988). That is a substantial decrease in steroids' dose needed per day to achieve the same therapeutic effect.

Beclomethasone, halogenated synthetic analog of cortisol used in a form of beclomethasone dipropionate (BDP) faces a similar problem. BDP is currently used for inhalation and as a nasal spray for treatment of bronchial asthma and seasonal and perennial rhinitis. Because beclomethasone dipropionate is poorly soluble in water, it is currently formulated as a microcrystalline suspension in halogenated alkane (Freon) propellants (PDR:1003 (1988).

The secondary adverse reactions following the use of these inhalers and sprays include localized infection of the mouth and pharynx with *Candida albicans* or *Aspergillus niger*, hoarseness and dry mouth. Simultaneous use of these steroids with other aerosols is not recommended due to potential toxicity from the inhaled fluorocarbon propellants. Further, tissue irritation has been reported due to drug crystallization and sedimentation during storage.

The advantages connected with using inhalation route rather than systemic administration are lessened by the necessity of multiple dosing. Such dosing is inconvenient, unpleasant, and may lead to nasal or oral mucosal tissue damage caused by repeated application of fluorocarbon, a drug carrying propellant, or by a solvent, or other additives necessary for nasal or oral inhalation administration.

Thus, it would be highly desirable to have a steroid formulation in the form of an inhalation system providing a sustained release of steroids where the number of inhalation administrations per day would be greatly reduced.

Other important routes of steroids' administration are intraarticular injection of steroid into inflamed joints and intrathecal injection of steroids into the brain and spinal cord during bacterial, inflammatory and viral diseases of the central nervous systems, nasal or oral administration during bacterial, viral or allergic reactions or cold symptoms, topical administration during dermatitis or bacterial infections, various parenteral administrations such as intravenous, intramuscular, intraperitoneal, subcutaneous or percutaneous for treatment of all kinds of infections, inflammations and allergic conditions.

All these routes of administration encounter the same problem. Either the doses of administered steroid are too large causing unwanted side effects or too low being insufficient for effective treatment of conditions needing treatment. Moreover, some of these routes of administration are extremely painful and unpleasant, for example intrathecal or intraarticular injections, and thus it would be of great advantage to have a steroidal formulation allowing sustained release of the drug which would eliminate a need for frequent and repeated injection or other dosing.

Moreover, as pointed out above, steroids, due to their chemical structure are poorly soluble in aqueous systems. Thus, in order to formulate steroid in an aqueous solvent it is necessary to add solubilizing agents such as ionic surfactants, cholates, polyethylene glycol (PEG), ethanol, and other solubilizers or use micronized suspension of crystalline drug. While in general these agents are considered pharmaceutically acceptable excipients, many of them have undesirable side effects particularly when used in inhalation, parenteral, intraarticular, intrathecal, nasal or topical formulations. The deleterious effect of agents such as PEG in membrane permeabilization and local irritation is well documented.

Therefore, it would be advantageous to provide steroid formulations without the necessity of adding such solubilizing agents and be able to provide for a permanent and stable supply of the drug to the organ or site of infection such as for example to generate submicron droplets by nebulization for deep lung penetration.

Certain improvements have previously been achieved by encapsulating steroids in conventional liposomes. For example, smaller doses of steroids were found to be effective when administered in liposome-encapsulated form. Also, modest prolongation of effect and restriction of the drug to the site of administration was achieved, and a marginal degree of decreased systemic uptake was accomplished.

Liposomes, lipid based drug carrier vesicles have recently emerged as a new technology in pharmaceutical sciences. Liposomes are composed of nontoxic, biodegradable lipids, in particular of phospholipids. Attempts have been made to prepare liposomes from nonphospholipid components which have the potential to form lipid bilayers that are more durable than conventional liposomes (Bioch. *Biophys. Acta.* 691: 227–232 (1982)). Currently, both conventional and nonphospholipid liposomes are rapidly becoming accepted as pharmaceutical agents which improve the therapeutic value of a wide variety of compounds.

Liposome drug delivery systems are reviewed in detail in *Cancer Res.*, 43:4730 (1983). In general, liposomes are advantageous in that they can provide controlled release of an entrapped drug, reduce side effects by limiting the concentration of free drug in the bloodstream, alter the tissue distribution and uptake of drugs in a therapeutically favorable way, and make therapy safer and more convenient by reducing the dose or frequency of drug administration.

Liposomes generally have been known to improve formulation feasibility for drugs, to provide prolonged sustained release, to reduce toxicity and to improve the therapeutic ratio, to prolong the therapeutic effect after each administration, to reduce the need for frequent administration, and to reduce the amount of drug needed and/or absorbed by the mucosal or other tissue.

Advantages such as decreased toxicity and degradation, use of smaller doses, the possibility of targeting the liposome towards a specific site, and reducing side effects of a liposome-bound cortisol over the use of a free or polymer-bound cortisol have been described in *Nature,* 271: 372–373 (1978).

The use of liposomes as a solubilizing agent for steroids in aqueous, nebulized inhalation suspensions essentially eliminates the use of potentially toxic halogenated hydrocarbon propellants and co-solvents such as ethanol. Such formulations also assure that the drug stays in a stable suspension, thus preventing the irritation caused by drug sedimentation and crystallization. Such irritation is often encountered with conventional steroidal suspension preparations. Notwithstanding the above, utilizing liposomes for inhalation formulations still face numerous problems. For example there is a little or no effect of liposomal entrapment on rapid systemic uptake, which remains unchanged indicating that even from the liposomes the steroid is still rapidly released so that the problem of unwanted side effects is not really eliminated by using the liposome formulations.

Because of their poor formulation properties, many useful steroids have had to be derivatized or modified so they could be accommodated within the chemical structure of the liposomes for enhanced retention. For example, 6–18 carbon-chain ester needs to be present in the steroid molecule for optimal lipophilic interaction between the water-insoluble corticosteroid and the lipid membrane.

The necessity for steroid modification is addressed in EPO application 85850222.2, which describes increased binding of the steroid to the liposomal membrane by derivatizing said steroid with a hydrophobic anchor, such as a fatty acyl chain. While the binding of derivatized drug to the membrane was shown to be somehow improved, the steroid derivative still did not sufficiently slow efflux rates of steroid from liposomes. This was due to the fact that the lipid composition of conventional, phospholipid liposomes does not provide a strong enough barrier to slow down the release of the derivatized steroid and to achieve prolonged release.

U.S. Pat. No. 4,693,999 discloses new steroid derivatives obtained by modification of corticosteroids, with fatty acid esters. These modified steroids incorporated in the lipid portion of liposomes for delivery via inhalation provided a prolonged steroid retention in the respiratory tract of experimental animals.

However, designing and synthesizing new steroid derivatives is inconvenient, costly, slow, laborious and often changes the drug efficacy. Thus, it would be greatly advantageous to provide a liposomal steroid formulation with substantially improved drug retention without need for drug modification.

Dexamethasone palmitate, a modified synthetic analog of cortisol, incorporated in liposomes was shown to surpass the effectiveness of microcrystalline cortisol acetate injection into arthritic joints of experimental animals. *J. Microencapsulation.* 4:189-200 (1987). However, although the formulation itself provided enhanced therapy against inflammation and diminished the leakage levels of the steroid into systemic circulation, the formulation was not therapeutically suitable because the charged carrier, necessary for the liposome formulation, proved to have cytotoxic effects.

Thus, many problems still remain unresolved with steroid formulations using conventional phospholipid liposomes. Some of these problems relate to the requirement for drug modification, poor drug loading into liposomes and poorly controlled release rate.

Water-insoluble steroids are generally difficult to load into conventional phospholipid liposomes because these molecules tend to crystallize rather than incorporate into the liposomal membrane. Such drug crystallization causes the same sedimentation problems and free drug toxicity upon administration as do non-liposomal steroidal suspensions. Modified steroids, unlike cholesterol which is ubiquitously distributed in biological membranes, in particular seem to be structurally or sterically incompatible with phospholipids in terms of hydrophobic or Van Der Waals interactions and thus crystallize out readily.

It would therefore be highly desirable to provide a formulation where the loading of the steroidal drug into liposomes would be improved and the crystallization problem avoided.

Previously available conventional liposomal steroidal formulations have also shown an uncontrollable and impractically fast release rate. Measurements of systemic uptake from the respiratory tract after inhalation of underivatized steroids formulated in conventional liposomes indicated little or no effect of liposomal entrapment on the release rate. This means that despite the liposome-binding, the drug was still released relatively quickly from the conventional phospholipid liposomes. This may be due to the fact that all steroids which are lipophilic in their nature tend to be released from the lipid membrane faster than water-soluble drugs encapsulated in the liposomes. *Biochem J.*, 158:473-6 (1976).

Thus, it would be greatly desirable to develop a pharmaceutically acceptable composition where the steroids could be formulated without the need of modifying or derivatizing the steroid itself, which at the same time could carry the greater amount of steroid and from which the steroid could be released with controllable and desired rate. The resulting composition would have to be capable of solubilizing the underivatized steroid, having highloading ability, prolonged sustained-release and stability.

It is the primary object of this invention to provide the liposome-steroid composition wherein the poorly water soluble or insoluble, sedimentation-prone, underivatized or unmodified steroids are successfully sequestered within the liposomal lipid vesicles of uniform and controllable particle size, having at the same time high encapsulation values, long-term stability, and effective sustained release with a controllable potency of the drug. The resulting composition would allow an administration of low doses of steroid thus reducing toxicity and systemic side effects while at the same time providing pharmacologically bioavailable doses of steroid in situ of the target organs. The composition would also be economically advantageous because it would effectively formulate all therapeutically needed steroid without loss occurring during the steroid formulation or during the therapeutical administration.

SUMMARY

One aspect of this invention is to provide nonconventional liposome based formulation for therapeutic delivery of various underivatized and unmodified steroids in the liposome vesicles of uniform and controllable particle size.

Other aspect of this invention is to provide formulation enabling liposome entrapment or encapsulation of underivatized steroids in the liposome vesicles of uniform and controllable particle size.

Still another aspect of this invention is to provide a liposome formulation with high encapsulation properties for encapsulating water-insoluble steroids.

Yet another aspect of this invention is to provide liposome/steroid composition which has lower toxicity, lower side effects, allows the targeting and release of steroid at a site of specific organ, removes need for multiple dosing, can be sterilized, and is sufficiently stable in dried form for long-term storage.

Another aspect of this invention is to provide controlled, sustained release of the steroidal drugs from the nonconventional liposome/steroid composition.

Still another aspect is to provide a process for making novel nonconventional liposome composition for controlled release of steroidal drugs.

Yet another aspect of this invention is to provide the method of use of the liposomal steroidal compositions for delivery by inhalation, intratracheal, peroral, parenteral, such as intravenous, intraperitoneal, intramuscular, subcutaneous, percutaneous, topical, intraarticular or intraventricular and ocular routes of administration.

DETAILED DISCLOSURE OF THE INVENTION

PREPARATION PROCEDURES

According to the present invention, it has been discovered that beclomethasone dipropionate and other steroids in underivatized form may be successfully retained in nonconventional liposomes for sustained release when the liposomes are formulated to contain a mixture of cholesterol and cholesterol salt such as for example sodium cholesterol sulfate, also known as cholesteryl sodium sulfate (cholesterol sulfate). Cholesterol sulfate or other cholesterol salt acts as a temporary barrier against drug efflux from the liposomes. To design the optimal formulation for high drug loading and sustained release of underivatized steroid, a number of different formulations were developed, studied, assessed and compared with compositions comprising components of the invention in various amounts and ratios as well as conventional phospholipid liposomes derived from egg, soybean, and synthetic phospholipids.

METHODS OF LIPOSOME FORMATION

The liposome suspension of the invention can be prepared by any of the standard methods for preparing and sizing liposomes. These include hydration of lipid films, solvent injection, reverse-phase evaporation and other methods, such as those detailed in *Am. Rev. Biophys. Bioeng.* 9:467 (1980). Reverse-phase evaporation vesicles (REVs) prepared by the reverse-evaporation phase method is described in U.S. Pat. No. 4,235,871, incorporated hereby by reference. The preparation of multi-lamellar vesicles (MLVs) by thin-film of a lipid film or by injection technique is described in U.S. Pat. No. 4,737,923, incorporated by reference. In two later procedures, which are generally preferred, a mixture of liposomeforming lipids dissolved in a suitable solvent is evaporated in a vessel to form a thin film, which is covered by an aqueous buffer solution. The lipid film hydrates to form MLVs, typically with sizes between about 0.1 to 10 microns.

Either the REVs or MLVs preparations can be further treated to produce a suspension of smaller, relatively homogeneous-size liposomes, in the 0.1-1.0 micron size range. Advantages of smaller, more homogeneous-size liposomes are, for example the higher density of liposome packing at a mucosal tissue surface, the higher concentration of liposome encapsulated drug transported to the target organ or tissue, or the greater optical clarity when applied topically to the eye. One effective sizing method involves extruding an aqueous suspension of the liposomes through a polycarbonate membrane having a selected uniform pore size, typically 0.2, 0.4, 0.6, 0.8 or 1 microns *Ann. Rev. Biophys. Bioeng.*, 9:467 (1980). The pore size of the membrane corresponds roughly to the largest sizes of liposomes produced by extrusion through that membrane, particularly where the preparation is extruded two or more times through the same membrane. A more recent method involves extrusion through an asymmetric ceramic filter. The method is detailed in U.S. Pat. No. 4,737,323, incorporated hereby by reference.

Alternatively, the REVs or MLVs preparations can be treated to produce small unilamellar vesicles (SUVs), large unilamellar vesicles (LUVs) or oligolamellar vesicles (OLVs) which are characterized by sizes in the 0.04-0.08 u, 0.1-0.5 u, and mixed micron range, respectively. Because of the small particle sizes, SUVs suspensions can be optically quite clear, and thus advantageous and preferred for example for ophthalmic applications or for such applications as the delivery of the steroid to the minuscule lung alveoli. Another advantage of SUVs, as suggested above, is the greater packing density of liposomes at a mucosal surface which can be achieved with smaller liposome particles, thus making SUVs preferred for inhalation, for treatment of deep lung diseases such as idiopathic infiltrative pulmonary fibrosis, degenerative interstitial pneumonia or for topical or nasal use.

The use of all SUVs, LUVs, MLVs, OLVs or mixture thereof is contemplated depending on intended therapeutic application and route of administration.

One preferred method for producing SUVs is by homogenizing an MLVs preparation, using a conventional high pressure homogenizer of the type used commercially for milk homogenization. Here the MLVs preparation is cycled through the homogenizer, with periodic sampling of particle sizes to determine when the MLVs have been substantially converted to SUVs.

The drug is encapsulated in the liposomes by using for example the procedure described in U.S. Pat. No. 4,752,425, incorporated by reference.

CONVENTIONAL AND NONCONVENTIONAL LIPOSOMES

As defined herein "the conventional liposomes" mean liposomes which contain phospholipids, and the "nonconventional liposomes" mean liposomes which do not contain phospholipids but are formed solely by cholesterol and cholesterol derivatives or, in alternative by amphipathic lipid components.

Both conventional and nonconventional liposomes can be formed by a variety of standard methods from a variety of vesicle-forming lipids. For the conventional liposomes these lipids include dialiphatic chain lipids, such as phospholipids, diglycerides, dialiphatic glycolipids, and cholesterol and derivatives thereof. The various lipid components are present in an amount between about 40-99 mole % preferably 60-90 mole % of the total lipid components in the liposomes, cholesterol or cholesterol derivatives are present in amounts between 0-40 mole %. In the nonconventional liposomes the cholesterol derivatives are present in amounts between 30-70:20-50:0.01-20 mole % of cholesterol derivative to cholesterol to drug, respectively. The drug encapsulated in both kinds of liposomes is in amounts of 0.01-20 mole %.

As defined herein, "phospholipids" include phosphatidic acid (PA) and phosphatidyl glycerol (PG), phosphatidylcholine (PC), egg phosphatidylcholine (EPC), lyso phosphatidylcholine (LPC), phosphatidylethanolamine (PE), phosphatidylinositol (PI), and phosphatidylserine (PS). These phospholipids may be fully saturated or partially hydrogenated. They may be naturally occurring or synthetic.

The liposome composition may be formulated to include minor amounts of fatty alcohols, fatty acids, and/or cholesterol esters or any other pharmaceutically acceptable excipients with the proviso that these minor lipid components do not significantly reduce the binding affinity of the liposomes for mucosal or organ tissue, are substantially unsaturated, and are not toxic or irritating.

PREPARATION OF NONCONVENTIONAL LIPOSOME COMPOSITION

Figure 1:
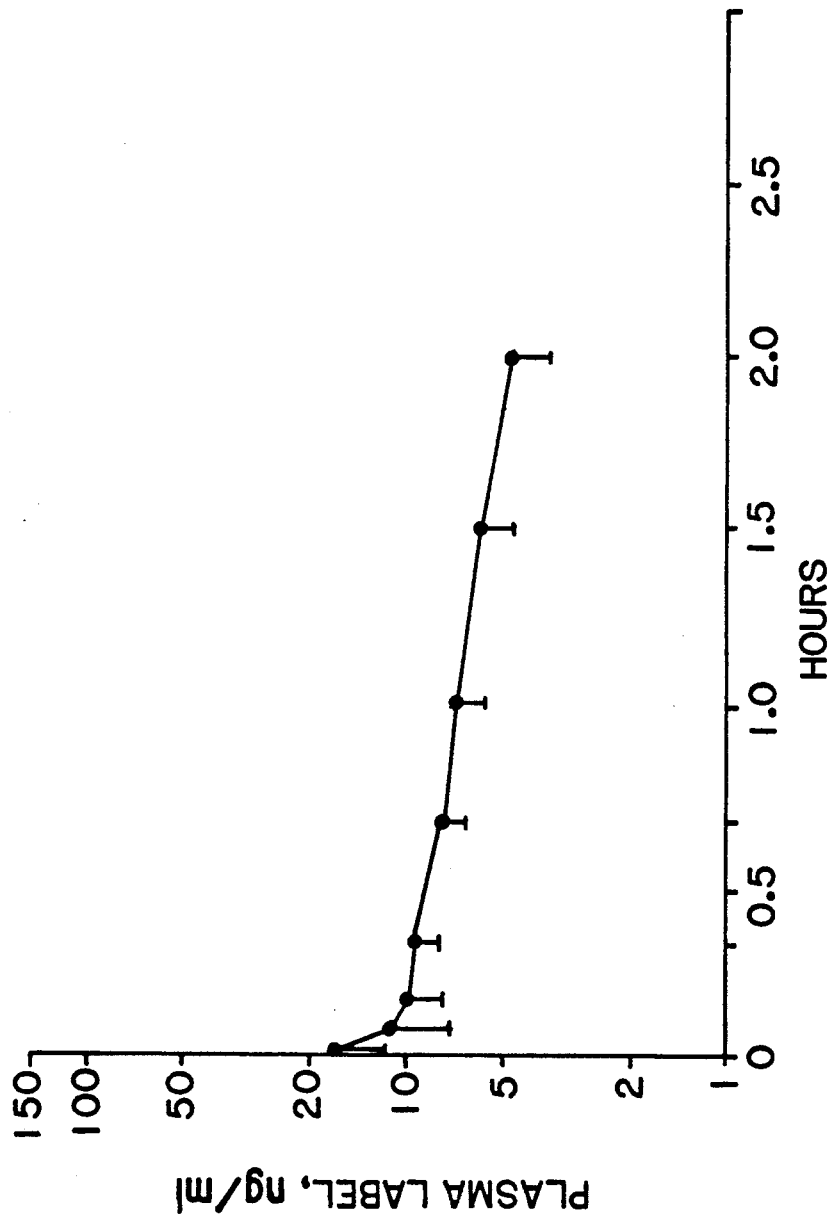
FIG. 1 shows the rat plasma concentration of BDP after intravenous injection of radiolabeled BDP.

According to the present invention, it has been discovered that BDP or other steroids in underivatized form may be successfully retained in liposomes, for delayed release when the liposomes are formulated to contain a high percentage of cholesterol salt, such as cholesteryl sulfate, typically from 30-70 mole %, preferably 50 mole % in combination with cholesterol, typically from 20-50 mole %.

According to one aspect of the invention, it has been discovered that the underivatized drug/cholesterol/-cholesterol sulfate composition of the invention has much improved properties such as lesser toxicity, decreased side effects, controllable sustained release, improved solubility, high encapsulation, steroid release at the target organ, absence of need for multiple dosing, extended stability in that it can be stored long-term in dried form without significant increase in particle size on rehydration.

To achieve all the above enumerated advantages, the current invention combines the lipid components including cholesterol with cholesterol salt, preferably cholesterol sulfate, providing the hydrophilic group, and the steroidal drug to be formulated to provide novel, highly efficient nonconventional liposomal composition for formulation of natural or synthetic underivatized steroids. The composition is engineered to have an increased drug loading and a controllable sustained release rate of the steroid drug. It also provides a means to solubilize the steroids and incorporate them in such liposomal composition without need to modify the drug. Further, the formulation can be easily sterilized thus meeting an important requirement for pharmaceutical preparations. It is also stable and suitable for long-term storage.

Lipid bilayers consisting entirely of cholesterol in their hydrophobic core can be conveniently constructed if a hydrophilic group is built in as part of the steroid molecule. Sodium salt such as sodium hydrogen sulfate, was used to provide such hydrophilic group. With equimolar amounts of cholesterol added, initially multilamellar liposomes form which then become unilamellar liposomes on prolonged sonication. The resulting nonconventional liposomal vesicles are comparable to those of conventional phospholipid vesicles in all aspects. Cholesterol bilayers possess internal barriers that are less easily permeated, thus allowing controllable sustained release of steroid from the core of liposomes. These bilayers can also keep steroidal drugs by hydrophobic and electrostatic interactions in bilayer leaflet thus providing slow release.

The composition of current invention comprises a lipid component, such as cholesterol, and cholesterol salt, and drug in ratio from 20-50:30-70:0.1-20 mole %. The best suited liposomal formulations for sustained release of the steroids were found to be cholesterol sulfate:cholesterol:steroid in mole % ratios of 55:40:10; 50:40:5; 53:37:9, most preferably 50:40:10 mole %.

A lipid composition containing cholesterol sulfate:cholesterol:BDP, at a mole ratio of 50:40:10 had the best delayed release of the drug when administered to the experimental animals by way of, for example, instillation in the respiratory tract.

All pharmaceutically acceptable cholesterol salts and excipients can be used in the formulation. While cholesteryl sodium sulfate (cholesterol sulfate) is preferred, the composition is not restricted to this particular salt and any other suitable cholesterol salt such as cholesterol nitrate, maleate, phosphate, acetate, and others can be advantageously used. In addition, the cholesterol sulfate sodium salt may be converted to other salts with different cations, which may include potassium, lithium, magnesium, and other divalent cations, tris, triethanolamine, ethanolamine, heterocycles and such other salts commonly used and pharmaceutically acceptable in pharmaceutical formulations.

Buffer used in the preparation of the nonconventional liposomes may be any buffer chosen from the group of citrate, carbonate, bicarbonate, acetate, Tris, glycinate, cacodylate, maleate, and such other, preferably phosphate buffered saline of pH 7.4.

Any organic aqueous solvent such as lower alcohols, dimethoxyethane, dioxane, tetrahydrofuran, tetrahydropyran, diethylether, acetone, dimethylsulfoxide (DMSO), dimethylformamides (DMF), and halogenated hydrocarbons, such as freon, acetonitrile, or mixtures of all those above, preferably chloroform/methanol are used in the process of generation of liposomes.

The method of preparation of nonconventional liposomes comprises of: 1) mixing dry cholesterol, cholesterol salt, preferably cholesterol sulfate, and steroid in amounts from 20-50 mole % of cholesterol, 30-70 mole % of cholesterol salt and 0.1-20 mole % of steroid, preferably 40 mole % of cholesterol, 50 mole % of cholesterol sulfate and 10 mole % of steroid; 2) dissolving the mixture in 5-30 ml of an organic solvent, preferably in 10 ml of methanol:chloroform (2:1 v/v); 3) repeatedly drying the obtained solution under nitrogen and/or vacuum, preferably three times or until the dried film forms on the bottom of the flask, or by lyophilizing the dry film for 10-180 minutes, preferably at 30 minutes, at temperatures of 18° C.-27° C., preferably at room temperature; 4) resuspending the residue in 1-10 ml of buffer at pH 7.3-7.5 preferably in the phosphate buffered saline, pH 7.4; 5) forming the liposomes by sonication, solvent injection or any other suitable method; 6) sizing the liposomes by extrusion, or by other methods; and 7) sterilizing the liposomes using the methods described above. Methods of preparing the composition of the invention are not limited to those named above, but all methods of liposome preparation such as solvent injection, thin film hydration, dry powder, reverse evaporation and others are equally suitable.

ENCAPSULATION VALUES

Drug encapsulation means the amount of the drug incorporated, loaded, associated, bound or otherwise attached to the liposomes or their bilayers. In general, the ability of liposomes to encapsulate drug is expressed in % of the starting amount. Thus, the optimal encapsulation of 100% is achieved where all drug is encapsulated in liposomes. Technically, however, it is often difficult to achieve 100% encapsulation because the encapsulation % depends on the lipid properties, on the drug properties and on the encapsulating method used.

The primary advantage of nonconventional liposomes is their high encapsulation value. The nonconventional cholesterol sulfate liposomes demonstrate higher drug loading with encapsulation values of 100%, when 10 mole % dose was used (total lipid concentration of 40 umol/ml) compared with conventional phospholipid liposomes, which generally allow only about 1 mole percent drug encapsulation at a total lipid concentration of 40 umol/ml. For example, unsaturated conventional liposomes without cholesterol have the flexibility of accommodating 1 mole percent of steroidal drug. This encapsulation value is too small. Saturated conventional liposomes composed of lipid such as fully hydrogenerated soy PC do not accommodate even small amounts of the steroidal drug. Formulations of steroids are thus difficult and a large amount of crystalline steroid could be detected after extrusion and on storage. Even though lyso PC containing liposomes can accommodate a steroid to fill in the acyl chain vacancy, such liposomes containing even as little as 2 mole percent of the steroidal drug exchange and release their drug readily, defeating thus the whole purpose of drug encapsulation in liposomes. (Table I).

Example 1, Table 1, illustrates the % encapsulation of steroid in the various conventional and nonconventional liposomes. While the % encapsulation for some conventional liposomes may seem high, the actual amount of drug which can be encapsulated in conventional liposomes (A-H) is about 10% of the amount of steroid which can be encapsulated in nonconventional liposomes (I-L).

STABILITY

Stability problems are also overcome in a current nonconventional liposome formulation, in terms of the sedimentation and crystallization problems encountered with nonliposomal or conventional liposome suspensions. Because of the unique cholesterol sulfate formulations which accommodate the drug by steric fit, and because of their high encapsulation and high retention values, drug crystallization does not occur outside or inside the liposomes, nor does sedimentation occur from the suspension. Such nonconventional liposomes are stable at 4° C. for up to 3 months and do not form the drug crystals.

According to one aspect of the invention, the nonconventional liposome composition may be prepared and stored as suspension, dry powder, dehydrated liposomes and as liposome paste. These liposome formulations provide the following advantages: relatively good stability on storage, a high drug capacity, a high ratio of liposome-entrapped to free drug, and very high viscosity for enhanced retention to the mucosal and ocular surface.

Methods for generating liposome pastes with up to 70% encapsulated aqueous volume have been described in co-owned U.S. patent application for "Liposome Concentrate and Method", Ser. No. 860,528 filed May 7, 1986, incorporated by reference. The concentrate is preferably formed by ultrafiltration with continued recycling of the liposome suspension material. These concentrates which have equilibrium maximal loading of steroidal drugs are stable for storage for at least three months at 4° C.

The dried particle (dry powder) liposome formulation can be prepared either by lyophilization of liposomes or spray drying. In the former method, the small-particle suspension is quick frozen and lyophilized or subjected to slow process lyophilization at a shelf temperature of preferably −20° C. or less.

For spray drying, the particle suspension is dried in a conventional apparatus in which the particles to be dried are sprayed in aerosolized suspension form into a stream of heated air or inert gas, and the aerosolized droplets are dried in the gas stream as they are carried toward a dry powder collector where the dried liposomesare collected. An exemplary spray dry apparatus is a Buchi 190 Mini Spray Dryer. BBA 897:331-334 (1987).

The drying temperature is at least about 25° C., preferably between about 30°-200° C. The temperature of the collection chamber is generally lower than that of the heated air, and typically about 30° C. The dried particles are collected and stored as a powder in dehydrated form, under an inert atmosphere in the presence of a desiccant. Such powders are storable under these indications for at least a year at ambient temperature. Dry powder compositions can be used as injectable materials after reconstitution or suspended in appropriate dilutants or freon propellants for aerosol administration or formulated to topical, nasal or oral dosage forms.

DETAILED DESCRIPTION OF DRAWINGS

Figure 2:
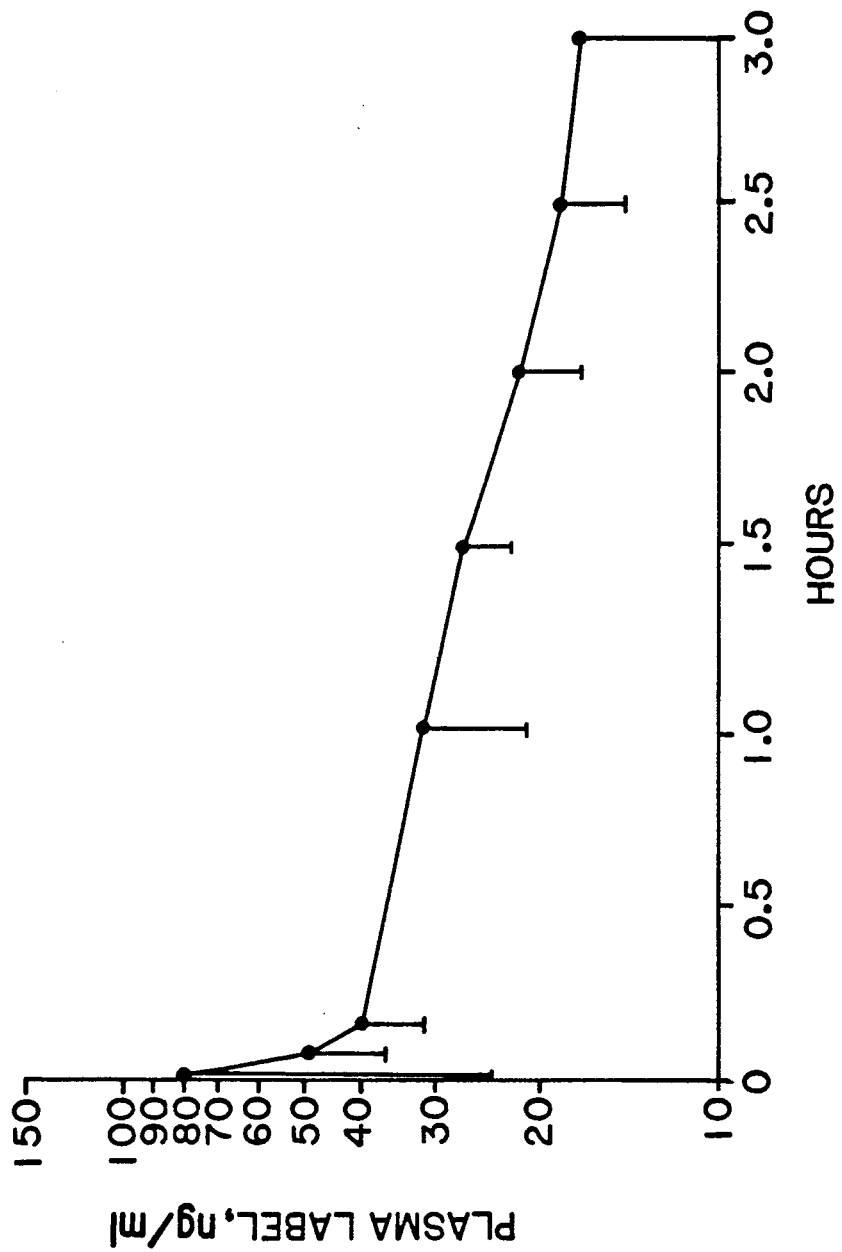
FIG. 2 shows the rat plasma concentration of BDP after intratracheal instillation of radiolabeled BDP.

In order to determine the rate of absorption of the steroidal drug into the plasma after intratracheal administration, various formulations containing either the free steroid or steroid encapsulated in liposomes were prepared and tested. Free steroid drug, in this case $^{14}$C labeled BDP, dissolved in ethanol/water (1:1) was administered to rats either intravenously (FIG. 1) or intratracheally (FIG. 2).

Figure 3:
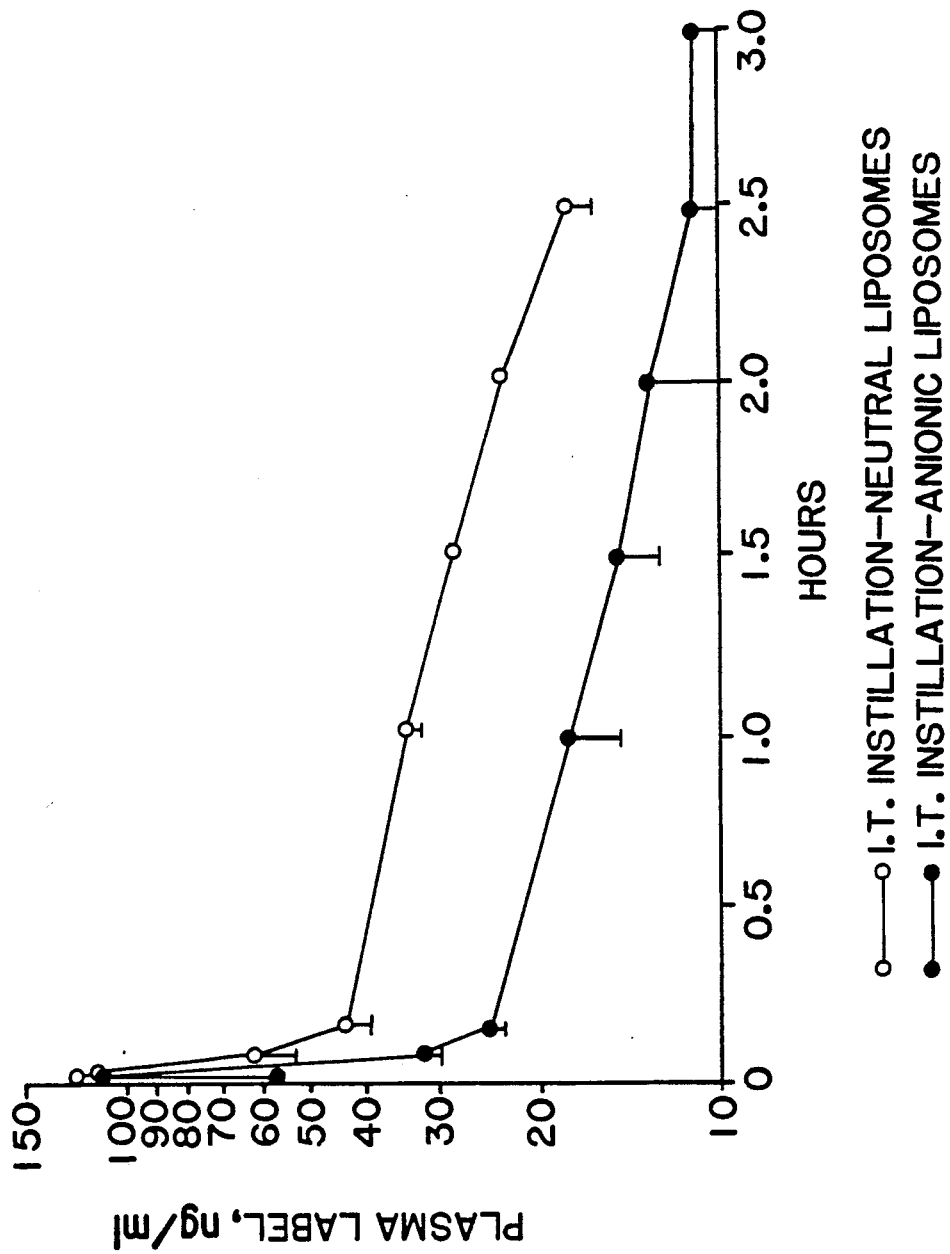
FIG. 3 shows the rat plasma concentration of BDP after intratracheal instillation of radiolabeled BDP encapsulated in two types of conventional liposomes.

The free drug control was administered intravenously to provide relative basis for measurement of bioavailability. Blood samples were taken at 5, 10, 20, 40, 60, 90 and 120 minutes and the radioactivity of radiolabeled BDP was determined using standard scintillation counting technique. The resulting plasma profiles, given in FIG. 1, illustrate the physiological removal of steroid from the blood circulation. In order to determine the plasma uptake of free steroid from lungs following the intratracheal instillation of radiolabeled $^{14}$C BDP, the same free drug formulation was instilled into rat lungs and the blood samples collected at intervals of 5, 10, 60, 90, 120, 150, 180 minutes. As will be seen from FIG. 2, the rate of absorption of free steroid from lungs to the plasma is rapid and the physiological removal from the plasma follows the same course as that of the free drug. When a similar experiment was performed with radiolabeled $^{14}$C BDP encapsulated in conventional anionic liposomes (EPC/EPG/BDP; 96:3:1) or in conventional neutral liposomes (EPC/BDP; 99:1), the rate of absorption was also rapid for both formulations (FIG. 3). Thus, the rate of absorption from lungs to plasma of free steroid and steroid encapsulated in conventional liposomes is not much different and follows similar curve.

Figure 4:
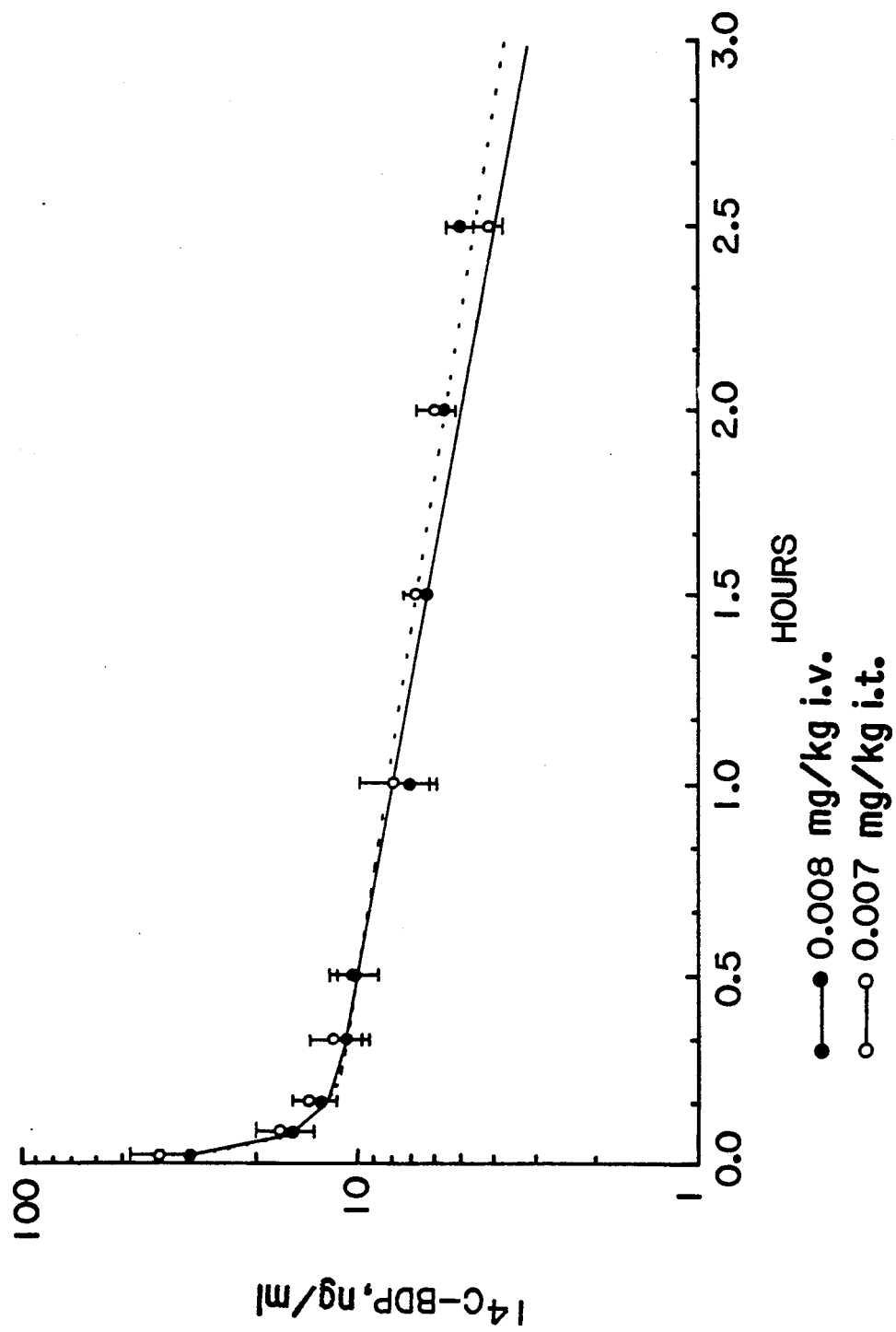
FIG. 4 shows the plasma kinetics of radiolabeled BDP after intravenous administration of free BDP and intratracheal instillation of radiolabeled BDP encapsulated in conventional cholesterol containing liposomes.

The pharmacokinetic parameters of free radiolabled $^{14}$C BDP (0.008 mg/kg in 50% ethanol) administered intravenously to a group of 12 rats, and intratracheally instilled radiolabed BDP (0,007 mg/kg) encapsulated in conventional liposomes (EPC:cholesterol sulfate:BDP;32:9:65.8:1.3) is illustrated in FIG. 4. The plasma kinetics of both free and encapsulated BDP in conventional liposome containing cholesterol sulphate and phospholipid is virtually identical, indicating that BDP is rapidly and completely absorbed from the lungs after intratracheal instillation of drug laden conventional liposomes.

Figure 5:
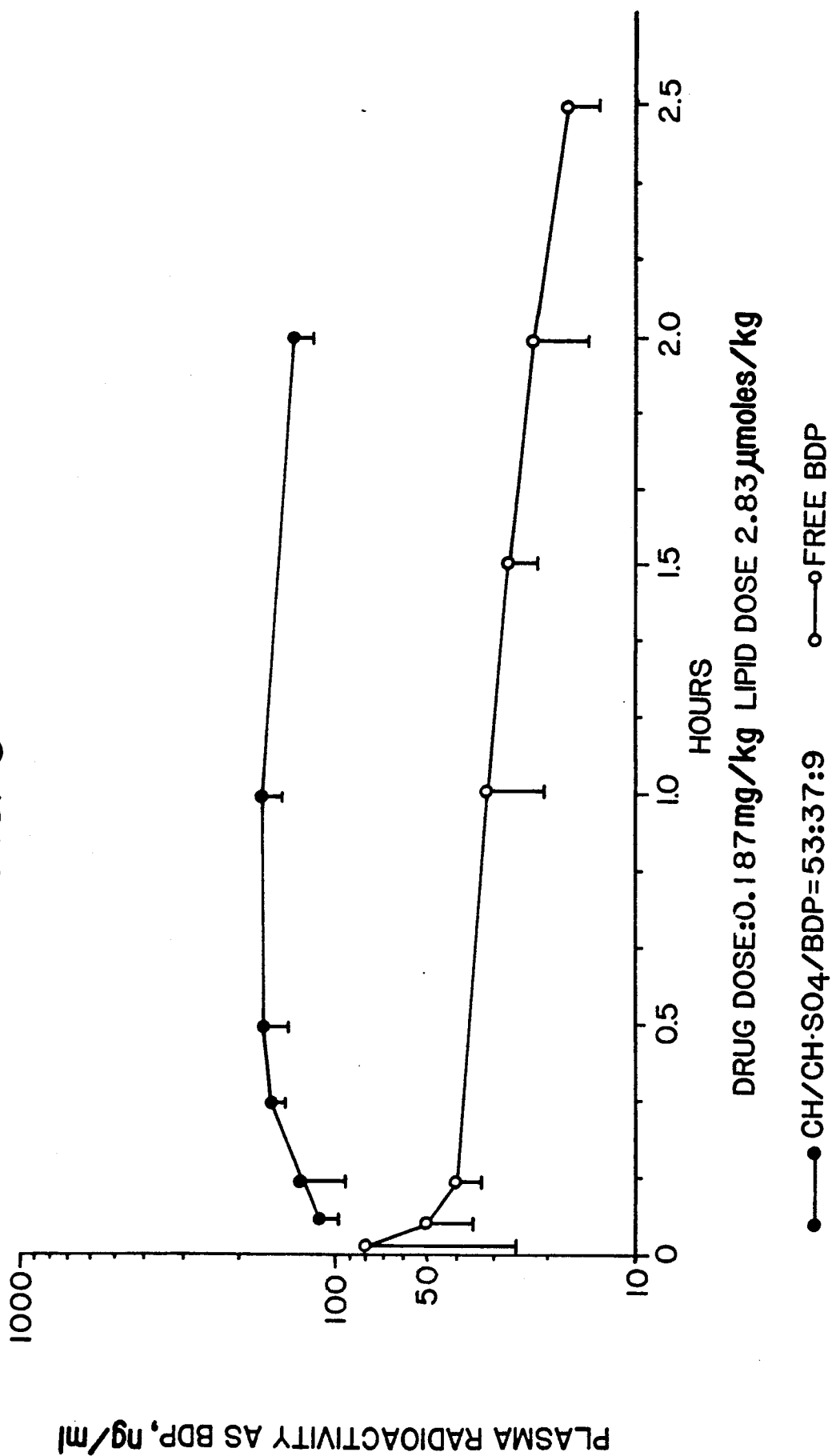
FIG. 5 shows the amount of plasma BDP radioactivity for two hours following the intratracheal instillation of nonconventional liposomal BDP illustrating sustained release and for three hours following the administration of free drug.

The delayed and/or sustained release of the steroid from the nonconventional liposome formulation containing combination of cholesterol/cholesterol sulphate and the steroid is shown in FIG. 5. FIG. 5 shows the plasma radioactivity of $^{14}$C BDP following intratracheal instillation of free $^{14}$C BDP and intratracheal instillation of $^{14}$C BDP encapsulated in nonconventional liposomes. While the free BDP is quickly removed from the lungs into plasma and metabolically eliminated, the rate of release of the liposomal BDP into the plasma is much slower. The concentration of $^{14}$C BDP in plasma initially increases, probably due to presence of some percentage of free BDP. Subsequently, it reaches and maintains certain plasma level equal to the rate of metabolic removal. In other words, after the first thirty minutes, the near equilibrium is reached in that the liposomal formulation releases only that much of the BDP into the plasma as is eliminated. Moreover, the nonconventional liposomes are able to sustain that level for measurable time. Pharmacokinetic properties of the steroidal drug are thus altered by drug incorporation into these liposomes.

Figure 6:
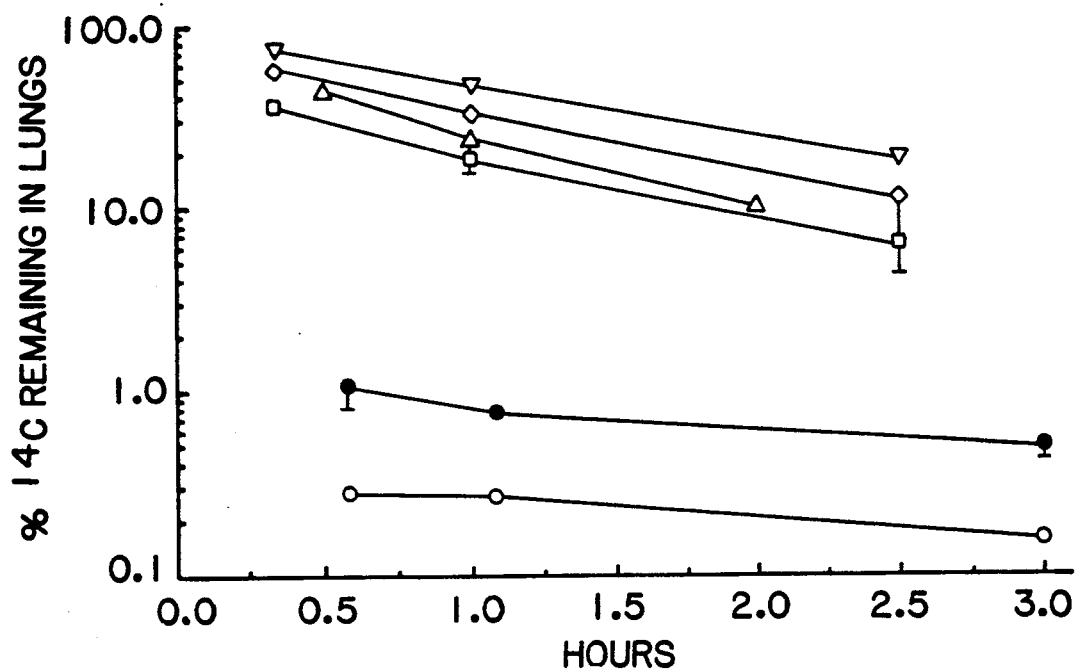
FIG. 6 shows the amounts of radiolabeled BDP remaining in the rat lungs following intratracheal instillation of five different liposome-encapsulated BDP formulations and the amount of the radiolabeled BDP in the lungs found after the intravenous administration of the free BDP.

Sustained release of four nonconventional liposome formulations, containing cholesterol sulfate/cholesterol/$^{14}$C BDP in various ratios namely 50:40:10 mole % with 0.260 mg/kg of BDP; 55:40:5 mole % with 0.260 mg/kg of BDP; 53:37:9 mole % with 0.187 mg/kg of BDP; and 50:40:10 mole % with 0.035 mg/kg of BDP was compared with the free BDP administered intravenously and with one formulation of conventional liposomes containing cholesterol sulphate/egg phosphatidylcholine/$^{14}$C BDP in ratio of 30:60:1.2 mole % with 0.007 mg/kg of BDP (FIG. 6).

Linear plots were obtained when the amount of radiolabel remaining in the lungs was plotted against time on semi-log paper, indicating that all four formulations were absorbed from the lungs by a first order process These data were fit by single exponential functions using a non-linear least squares curve fitting program (RSTRIP). The resulting slopes and intercepts were used as estimates of the absorption rate constant ($K_a$) and the amount of drug in the lungs at zero time, respectively. The absorption rate constants for the four cholesterol/cholesterol sulfate formulations ranged from 0.64 hr$^{-1}$▲, for 0.74 hr$^{-1}$■, for 0.84 hr$^{-1}$◆, for to 1.03 hr$^{-1}$▼; for corresponding to an absorption half-life of 0.68 hr, 0.78 hr, 0.89 hr, to 1.09 hr, demonstrating that sustained in vivo release of liposome-incorporated BDP had been achieved. The apparently longer half-lives for free $^{14}$C BDP (3.0 hr) and EPC/CH (2.4 hr) formulations shown in FIG. 6 are clearly not absorption half-lives since over 98% of the drug was absorbed before the first time point. These later values relate to the elimination of radiolabel already released from the liposomes and distributed to the lungs. The amount of drug in the lungs at time zero can be used to determine the amount of free drug in the formulation, since free drug is very rapidly absorbed from the lungs (Dose=free drug+amount in lungs at t=0). This amount also includes any liposome associated drug that was rapidly released ("burst" effect). The amount of drug present in the lungs at time zero ($T_0$) varied among formulations and was 90–48% for these nonconventional liposomes, although in vitro measurements by membrane exchange assay did not detect any free drug in the formulations. This would indicate that there are rapidly and slowly released pools of drug within each liposomal formulation.

The absorption kinetics (sustained release) was determined by measuring of percentage of $^{14}$C BDP remaining in the lungs following the intratracheal instillation of the above described five liposome formulations and one intravenous administration of free drug. In less than thirty minutes, 99.7% of free $^{14}$C BDP was removed from the lungs and 98.8% of the BDP encapsulated in conventional liposomes. In contrast, only 20% of radioactivity of $^{14}$C BDP encapsulated in the best nonconventional liposomes was removed from the lungs with 23% of radioactivity still being present at 180 minutes. The other three nonconventional liposome formulations also should sustain release of the steroid for the same time. Thus, the presence of cholesterol in combination with cholesterol salt and the absence of phospholipids is essential for sustained release of the steroid from the nonconventional liposomes.

Figure 7:
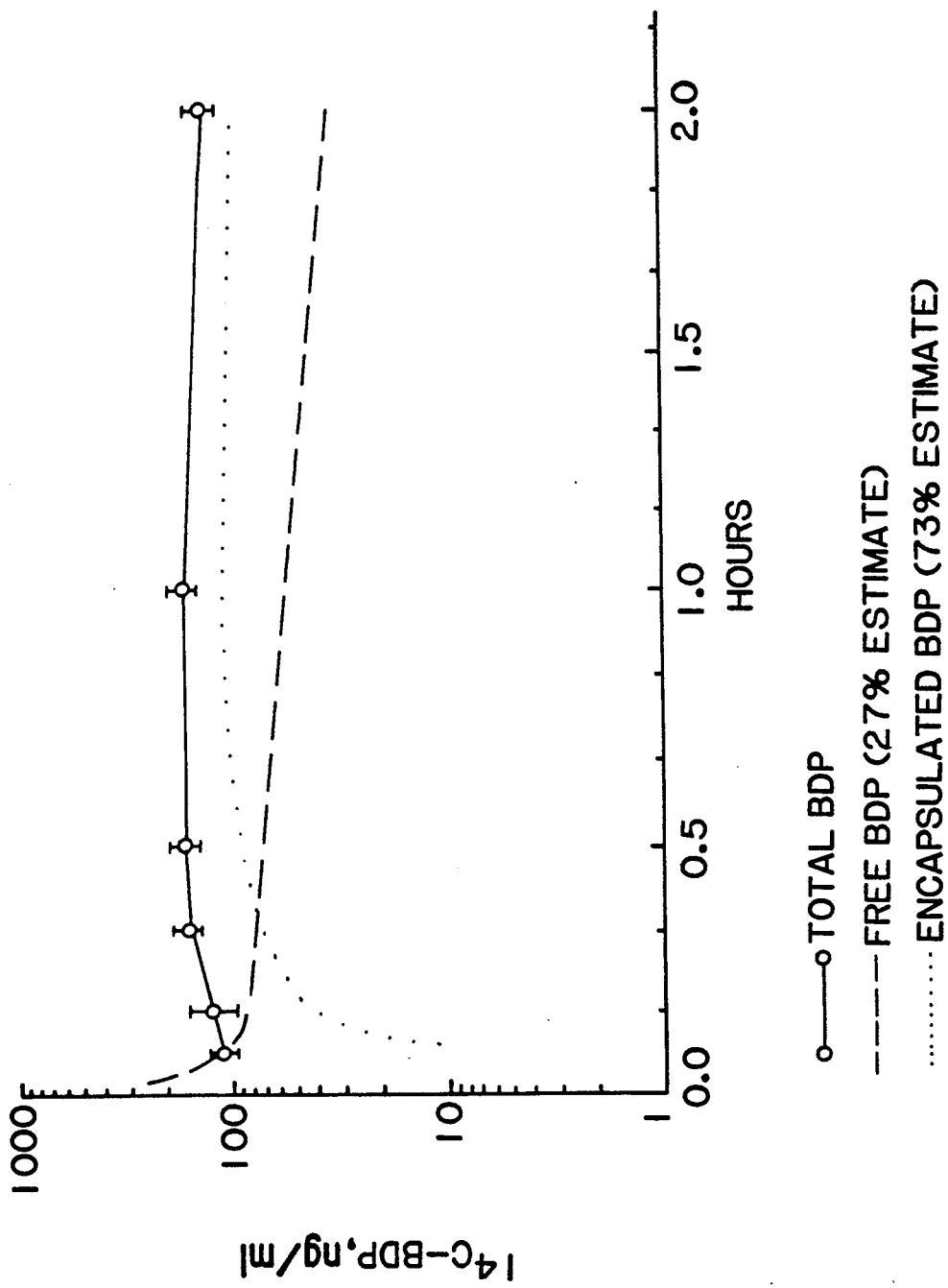
FIG. 7 shows the plasma concentration of free BDP and BDP encapsulated in nonconventional liposomes and the sustained release of liposome encapsulated BDP versus a total BDP.

Corresponding plasma concentration versus time data were obtained for one of the nonconventional sustained release formulations (FIG. 6). The plasma concentration versus time curve observed after administration of $^{14}$C BOP (0.187 mg/kg) in a cholesterol/cholesterol sulfate liposome formulation was strikingly different from that of free drug, remaining nearly flat over the two hour duration of the study (FIG. 5). Since lungs data indicated that 27% of the administered dose was free or rapidly released drug, the plasma concentration curve of FIG. 7 reflects the sum of concentrations due to "free" and "encapsulated" drug. The concentration time curve for "free" drug was estimated by assuming 27% of the dose was immediately absorbed and followed the kinetics observed for i.v. administration of free BDP. This curve was subtracted from the experimentally observed data to give an estimate of the plasma concentration due to liposomal sustained-release BDP (FIG. 7). It is clear that the plasma concentration versus time curve for the cholesterol/cholesterol sulfate formulations differ substantially from those observed following i.v. and conventional EPC liposome administration of BDP (FIG. 4).

In order to determine whether BDP was absorbed as unchanged drug or metabolized prior to release and absorption, lung samples from one study were analyzed by a thin layer chromatographic assay capable of separating BDP from its monopropionate hydrolysis products. The result showed no detectable metabolism of BDP prior to leaving the lungs.

The cholesterol sulfate and cholesterol are mandatory components of the nonconventional liposome formulation and are not inter-changeable with a phospholipids, normally used in conventional liposome compositions. The cholesterol is primarily responsible for, and greatly affects the sustained release, but the in vivo drugrelease half life depends on the relative amount of cholesterol sulfate and on the absolute presence of cholesterol in the composition. Drug release half life can be varied accordingly. For example, liposome composition containing egg phosphatidyl choline:cholesterol sulfate:BDP (60:30:10) has a drug-release half life in vivo only slightly lower than the conventional liposomes without cholesterol sulfate or the free drug, but it has pronounced drug retention in vitro compared to compositions without cholesterol sulfate (Example V and Table II). However, nonconventional liposome compositions containing cholesterol sulfate:cholesterol:BDP, (at a mole ratio 50:40:10; 55:40:5; 53:37:9 mole %) gave markedly delayed release in vivo of the drug when instilled in the respiratory tract of an experimental animal together with having much prolonged drug retention as compared to the retention of the free drug and conventional liposomes. (FIG. 6).

The plasma kinetics observed following the i.t. instillation of $^{14}$C-BDP (0.007 mg/kg) incorporated into conventional EPC:CHSO$_4$ liposomes (FIG. 6) were virtually identical to those observed following the i.v.

administration of a similar dose of free drug (FIG. 4). These data indicate that BDP formulated in conventional liposomes is rapidly and completely absorbed from the lungs after intratracheal instillation of this formulation. This is due to the incompatibility of the physical and molecular nature of the drug and bilayer architecture formed with phospholipids.

THERAPEUTIC APPLICATIONS

Therapeutic applications and advantages of the nonconventional liposomes and advantages are numerous. Sustained release of the drug from the nonconventional liposomes is expected to prolong the therapeutic activity after each administration, to reduce the frequency of administration, further improve the ratio of localized-to-systemic effects, and provide increased and extended local therapeutic effect in the lungs, joints, brain, spinal cord, blood, muscles, skin, mucosal tissue, eye, and other organs.

In addition, a sustained release formulation might reduce the amount of drug absorbed by the oral mucosa (due to the salivary action which would more likely clear aqueous liposome suspension into G.I.) thus reducing the incidence of oral or mucosal tissue infection following inhalation, nasal or peroral therapy. Topically administered to the skin of, for example lupus erythematosus patients, or patients with dermatitis or skin allergy, or topically administered to the eye for treatment of allergic and inflammatory conditions the formulation of current invention will provide a long term slow release of the steroid at a place where it is immediately active without need of having the whole body affected by the excess of steroid given systemically or without the need of readministration. Intravenously, intramuscularly or intraperitoneally it will provide a circulating reservoir of the drug to be released slowly to the blood stream and/or in the vicinity of the inflamed or infected organ. Intratracheally, the formulation will be delivered into the airways from which it can be slowly and continuously released to the bloodstream and can treat the inflammation of the airways, bronchitis, pneumonia, or tracheal allergic or infectious or inflammatory infections and conditions. Intrathecally, the formulation will deliver the steroidal drug into the brain, to the central nervous system and spinal cord. Such delivery is important for treatment of acute, subacute, or recurrent meningitis, encephalitis, aseptic meningitis, brain abscesses or spinal cord neoplasms. Intraarticularly, the formulation will be injected into joints for treatment of arthritis, gout, Lyme arthritis, osteoarthritis where the systemic cortiscosteroidal treatment is specifically contraindicated but intraarticular injections are beneficial albeit unpleasant and uncomfortable. The intraarticular injection of the nonconventional liposome steroidal formulation will avoid repeated injections because the formulation will be able to release the needed amount of steroid from the liposome for prolonged period of time.

The examples for providing the data and evaluating the novel composition in this application use primarily the anti-inflammatory steroid beclomethasone dipropionate, cortisone or hydrocortisone with inhalation, intravenous, intrathecal, intraarticular or topical routes of administration. The scope of the invention is not limited to BDP as a steroid, nor the described routes of administration but include all other steroids and all other routes of administration.

The invention is applicable, more broadly, to all steroids such as dexamethasone, aldosterone, betamethasone, cloprednol, cortisone, cortivazol, deoxycortone, desonide, dexamethasone, estroglones, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone, triamicinolone, testosterone or their respective pharmaceutically acceptable salts or esters.

Examples of the classes of compounds to be used in this composition to be administered through various therapies include, but are not limited to (1) bronchodilators, such as metaproterenol, sulfate, terbutaline, albuterol, bitolterol, pirbuterol, procaterol and salmeterol; (2) anti-inflammatory steroids, such as BDP, dexamethasone, prednisolone, hydrocortisone, fluoromethazone, medrysone, fluticasone, triamcinolone, and flunisolide; (3) cardiovascular steroids; (4) topical steroids; or (5) hormonal steroids all either alone or in combination. All these steroids and steroidal drugs may be administered in appropriate amount by the peroral, inhalation, intraperitoneal, intramuscular, subcutaneous, percutaneous, topical, ocular, intrathecal or intraarticular route of administration.

The increased retention of the steroid in the liposomes can be exploited in any type of delivery systems, such as inhalation, parenteral, intravenous or topical steroid administration and devices.

The liposomal composition of the invention is resilient, and can be prepared and delivered in a number of ways. For inhalation therapy, the delivery is achieved by (a) aerosolization of a dilute aqueous suspension by means of a pneumatic or ultrasonic nebulizer, (b) spraying from a self-contained atomizer using a propellant solvent with suspended, dried liposomes in a powder, (c) spraying dried particles into the lungs with a propellant or (d) delivering dried liposomes as a powder aerosol using a suitable device.

The improved retention of a steroid in the liposomes can be advantageously exploited in intravenous or topical delivery systems in devices, intravenous infusions, injections, capsules, cremes, drops, lotions, ointments. It can be used for injury or diseased conditions involving eye or skin wounds, rheumatoid arthritis, joint inflammation, allergic reactions, hormonal disturbances, asthma, emphysema, respiratory disease syndrome, cardiovascular disorders, infections, and other inflammatory conditions and allergic conditions.

The composition of the current invention shows a great stability, thus increasing a shelf-life of the drug for extended period of time.

An added benefit to the liposome delivery system is that it can be used for combination therapy. For instance, in certain asthmatic conditions, a steroid is used for antiinflammation, or as antiallergenic agent while a bronchodilator is needed to relax the bronchial muscle and expand the bronchial air passages. Both can be incorporated in the liposomes for slow release. Antibiotics, antivirals, antiallergens, vitamins, nutrients, or any other watersoluble compound can be used when dual therapy is needed to counteract the immunosuppressive characteristics of steroids.

The following examples illustrate methods of preparing nonconventional liposomes suitable for formulation of steroid drugs and for use of these nonconventional liposomes for therapeutic purposes. These examples are in no way intended to limit the scope of the invention.

EXAMPLE I

Preparation of Conventional Liposomes By Thin Film Hydration

This example illustrates preparation and encapsulation efficiency of conventional phospholipid liposomes incorporating steroid beclomethasone dipropionate (BDP).

Liposomes were formed by modified thin film hydration method according to BBA. 691:227 (1982). Unlabeled BDP obtained from Sigma was spiked with $^{14}$C-BDP. Labeled synthetic lipid dipalmitoylphosphatidyl choline $^3$H-DPPC (from New England Nuclear) in trace amounts was used as a lipid marker in addition to lipid determination by inorganic phosphate analysis. Conventional liposomal formulations containing steroid and phospholipid in the ratios indicated in Table 1 were prepared as follows:

A. 1 mole % of BDP spiked with $^{14}$C-BDP and 99 mole % of partially hydrogenated egg phosphatidylcholine spiked with $^3$H-DPPC were combined in a round bottomed flask, and dissolved in 5 ml of chloroform. The solvent was removed by a rotary evaporator at room temperature and vacuum dried for one hour under a lyophilizer. The residual thin dry lipid film was hydrated with 3 ml of phosphate buffered saline of pH 7.4 by placing the round bottomed flask on a rotary evaporator without vacuum for one hour at 30° and subsequently, under gentle shaking, on a mechanical shaker overnight at room temperature.

The MLV's formed were heterogeneous in size between about 0.05 to 20 microns, and a predominance of multilayered structures. These liposomes were extruded through a 0.4 or a 0.2 micron polycarbonate membrane by using a stainless steel extrusion cell (Lipex Biomembrane, Inc., Vancouver, British Columbia, Canada) to produce uniform homogeneous size distribution and to remove free drug crystals.

B. Using the procedure of Section A, 1 mole % of BDP, 96 mole % of egg phosphatidylglycerol and 3 mole % of egg phosphatidylcholine was formulated as formulation B.

C. Using the procedure of Section A, 10 mole % of BDP, 60 mole of egg phosphatidylcholine and 30 mole % of cholesterol sulfate was formulated as formulation C,.

Table I illustrates the encapsulation values and efficiency of various conventional and nonconventional liposome formulations.

TABLE I

| Formulation[5] Mole % | Drug/Lipid Ratio Initial[1] | Encap. Final[2] | Effic. |
|---|---|---|---|
| A EPC:EPG:BDP (96:3:1.3) | 0.013 | 0.011 | 85% |
| B EPC:BDP (98:2) | 0.020 | 0.015 | 75% |
| C EPC:BDP (95:5) | 0.050 | 0.020 | 40% |
| D PHEPC:BDP (99:1) | 0.010 | 0.008 | 80% |
| E PHEPC:BDP (99:1) | 0.010 | 0.010 | 80% |
| F DLPC:DLPG:BDP[3] (96:3:1) | 0.010 | 0.010 | 100% |
| G EPC:LEPC[4]:BDP (90:8:2) | 0.020 | 0.019 | 95% |
| H EPC:CHSO$_4$:BDP (60:30:10) | 0.100 | 0.012 | 12% |
| I CHSO$_4$:CH:BDP (53:37:9) | 0.090 | 0.090 | 100% |
| J CHSO$_4$:CH:BDP (50:40:10) | 0.100 | 0.100 | 100% |
| K CHSO$_4$:CH:BDP (55:40:5) | 0.050 | 0.050 | 100% |
| L CHSO$_4$:CH:BDP (50:40:10) | 0.100 | 0.100 | 100% |

[1]Amount formulated.
[2]After formulation and removal of non liposome associated free drug.
[3]DLPC and DLPG refer to dilauroyl phosphatides.
[4]LEPC refers to lyso egg phosphatidylcholine.
[5]All liposomes were formulated at 40 u mole/ml total lipid concentration.

initial drug/lipid ratio refers to percent mole fraction of the drug used in the formulation. The final drug/lipid ratio means mole % from fraction of drug in liposomes after formulation and removal of free drug not associated with liposomes. The encapsulation efficiency shows the amount of the steroidal drug which can be encapsulated in various nonconventional (I-L) or conventional (A-H) liposomes. As can be seen the conventional phospholipid containing liposomes can have rather high encapsulation efficacy with respect to limited amount of drug used in the formulation. But final drug/lipid ratio shows that only 2 mole % of drug could be incorporated into these liposomes at total lipid concentration of 40 umole/ml.

Nonconventional liposome formulations prepared as described in Example III below, show high encapsulation efficiency at high drug concentration. The overall encapsulation of steroid in nonconventional liposomes was around 100% even when 10 mole % drug was used in the formulation with requirement for the amount of lipid approximately 10 times lower than for conventional liposomes.

Beclomethasone dipropionate phospholipid liposome formulations were tested for their release behavior in an in vitro and in vivo exchange with membrane systems as described in Examples V and VI.

EXAMPLE II

Preparation of Conventional Liposome Formulation by Solvent Injection Technique

This example describes the preparation of conventional liposomes using the procedure described in U.S. Pat. No. 4,235,871.

A. A mixture of partially hydrogenated egg phosphatidylcholine (PHEPC IV-40, 1.98 mmol), and steroid (BDP, 0.02 mmol), in the mole ratio of 99:1 was spiked with radioactive label as in Example I.A. and dissolved in 100 ml of Freon 11 containing 1.0 ml of ethanol. Liposomal BDP dispersion was formed by slowly injecting the lipid/drug/freon solution into 50 ml of the phosphate buffered saline pH 7.4 under the following conditions: Injection rate: 1.25 ml/min; Vacuum: 400 mm Hg; Temperature: 20° C.; Mixer rate: 1000 rpm. After the injection was completed, the vacuum level was adjusted to 150 mmHg for about 30 min to remove residual solvent. Liposomes thus formed were extruded through a 0.4 or a 0.2 micron polycarbonate membrane to produce uniform size liposome distribution and to remove free drug crystals. Resulting liposomes were submitted to in vitro exchange assay described in Example VI.

B. Using the procedure of Section A, 1 mole % of BDP, 96 mole % of egg phosphatidylcholine and 3 mole % of egg phosphatidylglycerol was formulated as formulation B.

C. Using the procedure of Section A, 10 mole % of BDP, 60 mole % of egg phosphatidylcholine and 30 mole % of cholesterol sulfate was formulated as formulation C, substituting freon with solvent alcohol/freon or alcohol/chloroform (2:1).

EXAMPLE III

Preparation of Nonconventional Liposomes

This example illustrates the method for preparing the nonconventional cholesterol, cholesterol sulfate containing liposomal composition for sustained release of steroids.

$^{14}$C-BDP used as a marker in formulations was obtained by conversion of $^{14}$C sodium propionate (1 mCi, Sp. Act. 56 mCi/mmol) to propionic anydride which was used to acylate nonlabeled beclomethasone in the presence of acylation catalyst dimethylaminopyridine. $^3$H-cholesterol sulfate was synthesized according to a scaled-down and modified version of Mandel procedure described in *Biochem. Zeit.* 71:186 (1915).

A. Steroidal drug BDP (10 mole %) and lipids cholesterol sulfate (50 mole %) and cholesterol (40 mole %) in amounts (40 u mole/ml per liposomal formulation) were dissolved in 10 ml methanol:chloroform (2:1), added to a screw-cap test tube and dried under nitrogen. The procedure was repeated three times and the dried film was lyophilized for half an hour at room temperature. Depending on the liposomal volume needed, the residue was resuspended in about 2 to 5 ml of phosphate buffered saline (pH 7.4, mOsm—295, originally preserved with sodium azide) and sonicated with a bath sonicator (Model GI12SPIT, 600 volts, 80 KC, 0.05 Amps) for half an hour to prepare multilamellar vesicles (MLVs). An aliquot of the sonicated, pre-extruded MLVs sample was saved and volume of preparation recorded for determination of baseline values. Liposomes were then extruded with a stainless steel Cullis high pressure extrusion cell one time through a 8.0 um Nucleopore polycarbonate membrane and two times through a 0.4 um Nucleopore polycarbonate membrane at ≦500 psi using the extrusion method described in U.S. Pat. No. 4,737,323.

A post-extrusion sample was saved to determine the amount of drug or lipid lost in the sizing process. Post-extrusion volume was noted. Free drug, if any, was removed by repeated washing with phosphate buffered saline and centrifugation. Liposomes were centrifuged three times on the Beckman L8-70M Ultracentrifuge at temperature of 4° C., at 47,600 rpm, for 1 hour, using 50 Ti rotor. The supernatant was discarded and the pellet resuspended in a volume equal to the post-extrusion volume after each centrifugation. The cleaned sample obtained by resuspending the pellet after the third centrifugation was labeled as To sample. This sample was saved to determine percent encapsulation.

All liposome formulations I-L (Table I) were prepared according to this procedure.

B. Using the procedure outlined above, dexamethasone, hydrocortisone, prednisolone, fluoromethasone, medrysone, and all other steroids are similarly formulated in nonconventional liposomes.

EXAMPLE IV

Encapsulation Efficiency and Stability

This example illustrates lipid compositions screened by varying the level of drug BDP, by determining the amount of the drug incorporated into the liposomes i.e. drug encapsulation, and by monitoring the stability of drug that remains associated with liposomes over time. (Table I)

Multilamellar vesicles (MLVs) were formed containing $^{14}$C BDP in phosphate buffered saline at pH 7.4 and extruded through a 0.4 micron polycarbonate membrane as described above in Example I. The samples were washed and centrifuged several times to remove the free drug that is not associated with the liposomes according to Examples 1–3.

The vesicles were visually examined under a light microscope to detect the presence of drug crystals. No crystals were observed after encapsulation of steroidal drug BDP into nonconventional liposomes. Conventional liposomes had to be washed to remove the excess of the drug before they were microscopically clear of crystals. In addition BDP incorporation was low.

The level of incorporation of the drug in the liposomes was determined based on radioactive counts and expressed as encapsulation efficiency as shown in Table I.

The stability of the incorporated steroidal drug in the liposomes was followed for several days to several months. For these stability studies, liposome samples obtained above were further diluted with PBS at pH 7.4 (1:5 v/v) and incubated at ambient temperature. Time aliquots were withdrawn and pelleted by centrifugation (19,000 rpm, 4° C., 30 min). The supernatant and pellets were monitored for the presence of lipid and drug. After the liposome preparations were diluted, the amount of drug remaining in the liposomes after three days to three months was determined to assess the stability of the incorporation. Very little, if any, of the steroid leaked out of the nonconventional liposomes after three days indicating that the incorporation was very stable at ambient temperature.

Nonconventional liposomes also showed no crystals after three months of storage at 4° C. by light microscopy. Conventional liposomes, although appearing stable for 3 days at ambient temperature in buffer solutions, lost readily their drug content during the longer period of storage and/or in the presence of an acceptor membrane. Conventional liposomes such as A-G (Table I) even though they showed no crystals after 3 months at 4° C., readily lost the drug content both in vitro in the presence of a membrane reservoir (Table II) and in vivo.

EXAMPLE V

In Vitro Membrane Exchange Assay

This example illustrates the sustained release from the

EXAMPLE V

In Vitro Membrane Exchange Assay

This example illustrates the sustained release from the nonconventional liposome formulations prepared according to the current invention.

An in vitro membrane exchange assay for measuring the release of drug from liposomes was established for screening of all formulations before conducting bioavailability studies.

BDP, as a steroid poorly soluble in water, and is primarily entrapped in the lipid bilayer rather than in the aqueous core of liposomes. Thus, very little of the drug can be released into a surrounding aqueous environment unless a huge volume of buffer is used based on partitioning characteristics of the drug. Since BDP has good solubility in phospholipid membranes, liposomal BDP may be rapidly exchanged from the bilayer of liposomes to surrounding cell membranes in the lung. To mimic the cell membranes in the lung, in vitro system was set up using small unilamelar vesicles (SUVs).

An aliquot of conventional liposome formulation of BDP (EPC:EPG:$^{14}$C-BDP/96:3:1) prepared in Example I was mixed with an equal volume (50:50) adjusted to the same total molar lipid amounts of non-drug containing empty EPC SUVs' prepared according to procedure of Example I with EPC as the only lipid. Both, drug containing and empty liposomes (MLVs or SUVs), were mixed and incubated at 37°. Samples were taken at 0, 0.5, 1, 2 and 4 hours. Samples were centrifuged at 4° C. for one hour to separate the drugcontaining liposomes (pellet) and the empty SUVs liposomes (supernatant). Pellets and supernatants were analyzed for radioactivity. Approximately half of all radioactivity was found in the supernatant for all time points, indicating that the drug was rapidly transferred from the drug-containing conventional liposomes to the empty SUVs until an equilibrium was reached between the two types of membranes.

This experiment was done with formulations EPC:EPG:BDP (96:3:1) and PHEPC:BDP (99:1). Both these formulations (Table II, A and B) had a high percentage of the drug exchanged from drug containing liposomes to empty SUVs, namely 89% for EPC:EPG:BDP and 85% for PHEPC:BDP.

Because of the rapid transfer of BDP into the SUVs, only the initial time point was used in subsequent studies. The ratio of drug-containing to non-drug containing liposomes was varied from 1:1 to 1:25. Results showed that at a ratio of 1:5 (donor/acceptor liposomes) bulk of the drug was rapidly exchanged to acceptor membranes.

The same method was then used to measure the amount of drug released from three nonconventional liposome formulations of BDP (Table II, D-E) and one conventional liposome formulation containing cholesterol sulphate (Table II C). From three nonconventional liposome formulations containing cholesterol sulfate, CH:$CHSO_4$:BDP 40:50:10; 40:55:5 and 37:53:9 mole %, none of the drug was released. Conventional phospholipid liposomes containing cholesterol sulfate (EPC:$CHSO_4$:BDP/60:30:10) which were not able to incorporate more than 1.2 mole % of the drug, released 9% of the incorporated drug to the acceptor SUVs. These vesicles also behaved like conventional liposomes types in animal models (Example VI).

From the formulations containing combination of cholesterol sulphate and cholesterol with steroid, none of the drug was released into the supernatant and thus no drug was transferred between drug containing liposomes and empty liposomes.

TABLE II

Results of In Vitro Membrane Exchange Assays

| Formulation | Percent of Drug Transferred |
|---|---|
| A. EPC:EPG:BDP (96:3:1) | 89% |
| B. PHEPC:BDP (99:1) | 85% |
| C. EPC:$CHSO_4$:BDP (60:30:10) | 9% |
| D. $CHSO_4$:CH:BDP (50:40:10) | 0% |
| E. $CHSO_4$:CH:BDP (55:40:5) | 0% |
| F. $CHSO_4$:CH:BDP (53:37:9) | 0% |

EXAMPLE VI

In Vivo Studies

This example illustrates the in vivo studies with nonconventional liposomes and their potential for sustained release.

All studies were performed in male Sprague-Dawley rats weighing 250 to 450 g. After fasting for 16 hours, animals were anesthetized by i.m. injection of ketamine (25 mg/kg), xylazine (5 mg/kg) and acepromazine (0.5 mg/ml). During the procedure the animal's body temperature was maintained with a 37° C. heating pad. Additional anesthetic was administered as required, using half the original dose. A midline incision was made in the neck and the right jugular vein and left carotid artery were cannulated with short lengths of polyethylene tubing to which a 23 ga Luer stub adapter (Clay Adams #7565) and plastic 3-way stopcock (Argyle #173518) were attached. Blood samples (0.5–4 ml) were removed from the carotid arterial cannula after first flushing with fresh blood to clear the line. Blood volume removed was replaced with an equal volume of 5% dextrose solution containing 50 U/ml of heparin via the jugular cannula. For intravenous (i.v.) injection studies, drug was injected into the venous cannula with a 500 ul glass syringe via a 22 ga needle and injection cap and flushed with 0.5 to 1.0 ml dextrose solution.

For intra-tracheal (i.t.) instillation of BDP formulations, (Table III) the trachea was cannulated with a 4 cm long section of Teflon tubing (1.2 mm I.D.), inserted at the level of the fifth tracheal ring below the thyroid cartilage and tied in place with a suture. Excess fluid in the trachea was aspirated through tubing attached to a syringe. A 0.5 ml glass syringe with a blunt needle and short length of polyethylene tubing attached was used to administer the formulations. The tubing was inserted to the level of the bronchial bifurcation and the dose (100 to 400 ul) rapidly administered during an inhalation. Animals were supported head up on a tilted dorsal support (approximately 70°) during the instillation process.

Blood samples were removed at four time points during the study from each rat, centrifuged, and the serum was removed and stored frozen (−20° C.) until assayed. Lung tissue samples were collected by rapidly excising the lungs after the final blood sample and immediately homogenizing in ice-cold acetonitrile (10.0 ml). The homogenate was briefly centrifuged and measured aliquots of the supernate removed to Teflon-stoppered glass tubes which were stored at −20° C. or below until assayed.

Analysis of plasma and lung tissue samples for $^{14}$C-BDP was carried out by liquid scintillation counting. The actual dose administered in each study was determined by measurement of duplicate dose control samples of the formulation which were delivered by the same apparatus used in dosing the animals.

TABLE III

Intratracheal Instillation to Sprague-Dawley Rats.

| Liposome Formulation (mole %) | Dose BDP (mg/kg) |
|---|---|
| $CHSO_4$:EPC:BDP 32.9:65.8:1.3* | 0.007 |
| $CHSO_4$:CH:BDP 53:37:9 | 0.187 |
| $CHSO_4$:CH:BDP 50:40:10 | 0.260 |
| $CHSO_4$:CH:BDP | 0.260 |

TABLE III-continued

Intratracheal Instillation to Sprague-Dawley Rats.

| Liposome Formulation (mole %) | Dose BDP (mg/kg) |
|---|---|
| 55:40:5 | |
| CHSO$_4$:CH:BDP | 0.035 |
| 50:40:10 | |

*This formulation was prepared at 60:30:10 (molar ratio). Since BDP was incorporated only to the extent of 1.2 mole % of original amount, the ratios were adjusted accordingly.

Each of the liposomal BDP formulations shown in Table III was administered to a group of 12–18 rats as described above. Groups of 3–6 rats were sacrificed at each of three time points during each study and the amount of radiolabeled BDP remaining in the lungs was measured by liquid scintillation counting. In some studies, the plasma concentration of radiolabel was also measured over the course of the experiment.

The pharmacokinetic parameters of free BDP were determined following intravenous administration of $^{14}$C-BDP (0.008 mg/kg in 50% aqueous ethanol) to a group of 12 rats. Plasma and lung levels of radiolabel were measured as previously described. The decrease in plasma concentration versus time following free drug administration was biphasic (FIG. 4). These data were subjected to analysis by a non-linear least squares curve fitting program (RSTRIP, MicroMath, Salt Lake City, Utah) and the resulting exponential slopes and intercepts interpreted according to a two compartment open pharmacokinetic model.

The plasma kinetics observed following the i.t. instillation of $^{14}$C-BDP (0.007 mg/kg) incorporated into EPC/cholesterol sulfate liposomes were virtually identical to those observed following the i.v. administration of a similar dose of free drug (FIG. 4). The amount of radiolabel remaining in the lungs after 35 minutes was only 1% of the total administered dose for this formulation (FIG. 6). These data indicate that BDP is rapidly and completely absorbed from the lungs after instillation of this formulation.

The absorption kinetics of nonconventional liposomal formulations were found to differ significantly from those of free drug and formulation containing EPC and cholesterol sulfate (FIG. 6). Significant amounts of radiolabel were detected in the lungs over the course of the study for each of the four cholesterol/cholesterol sulfate formulation studied. In contrast, 98.8% of the $^{14}$C-BDP in EPC/CHS liposomes had left the lungs 30 minutes after administration and 99.7% of free $^{14}$C-BDP was absorbed in the same time period. These results demonstrate that sustained in vivo release of liposome incorporated BDP had been achieved.

Corresponding plasma concentration versus time data were obtained for one of the sustained release formulations (FIG. 7). The plasma concentration versus time curve observed after administration of $^{14}$C-BDP (0.187 mg/kg) in a cholesterol/cholesterol sulfate liposome formulation was strikingly different from that of free drug, remaining nearly flat over the two hour duration of the study (FIG. 6). Since lung data indicated that 27% bf the administered dose was free or rapidly released drug, the plasma concentration curve for this study reflects the sum of concentrations due to "free" and "encapsulated" drug. The concentration time curve for "free" drug was estimated by assuming 27% of the dose was immediately absorbed and followed the kinetics observed for i.v. administration of free BDP. This curve was subtracted from the experimentally observed data to give an estimate of the plasma concentration due to liposomal (sustained-release) BDP (FIG. 7).

The present study shows that the lipophilic steroid beclomethasone dipropionate can be successfully incorporated into a nonconventional liposomal formulation that provides sustained in vivo release of the drug following intratracheal instillation.

Table IV illustrates the in vitro and the in vivo exchange of conventional and nonconventional liposomes.

TABLE IV

| Formulation | In Vitro Exchange | In Vivo Exchange |
|---|---|---|
| EPC:BDP (98:2) | + | + |
| EPC:EPG:BDP (96:3:1) | + | + |
| EPC:CHSO$_4$:BDP (50:40:10) | − | − |
| CHSO$_4$:CH:BDP (53:37:9) | − | − |
| CHSO$_4$:CH:BDP (55:40:5) | − | − |

EXAMPLE VIII

Preformulation Studies

This example determines the localization of the steroid in the liposomal structure and illustrates the steroid's water insolubility.

Beclomethasone dipropionate is a lipophilic drug. The solubility of the drug in different solvents is listed below:

| Solvent | Solubility |
|---|---|
| Ethyl Alcohol | 16.7 mg/cc |
| Chloroform | 125 mg/cc |
| Acetone | Highly soluble |
| Water | 54.4 ug/cc* |

*determined using radiolabeled material.

The partition coefficient for beclomethasone dipropionate between octanol and phosphate buffer saline was determined at pH 7.4. Nearly all (95%) of the BDP was associated with the octanol. This indicates that the drug will most likely reside in the membrane core of the bilayer.

EXAMPLE VIII

Intrathecal Administration of Liposomal Steroids

This example illustrates the intrathecal administration of the steroids formulated in nonconventional liposomes. The treatment is useful for boosting the effect of antibiotic or other treatments in severe sepses, blood poisoning, meningitis, brain inflammations and infections or other conditions when the immediate and prolonged administration of the steroid is indicated.

Male Sprague Dawley rats, 3 to 5 months old, weighing between 360–460 grams are anesthetized with sodium pentobarbital (45 mg/kg;i.p.) and mounted in a conventional stereotaxic frame. A midline incision is made to expose the dorsal surface of the skull. A small hole (1 mm) is drilled through the calvarium at a point 0.4 mm rostral and 1.8 mm lateral to the bregma. The dura is torn with a sharp needle and a 30 gauge blunt needle tip is lowered into the brain to a point 4.2 mm below the skull surface into a lateral ventricle.

The rats are divided into one experimental and one control group. The experimental group is injected with 50 ul of liposomal cortisone composition of 50 mole % of cholesterol sulfate, 40 mole % of cholesterol and 10 mole % of cortisone (spiked with radioactive cortisone) prepared according to procedure of Example III. The control group is injected with 50 ul of the free cortisone 20 mg/ml suspended in 0.9% NaCl. Injection is done over 25 minutes using a syringe infusion pump. At the end of the injection, the needle is removed and the skin defect is closed with a surgical staple.

At appropriate time points, three rats per time point from each group are sacrificed with an overdose of sodium pentobarbital (100 mg/kg i.p.), the blood specimens are obtained from cardiac puncture and the animals are allowed to exanquinate completely. The skin overlying the calvarium is removed and the calvarium is carefully removed. 20 ul of cerebrospinal fluid is obtained by carefully making the small tear in the underlying dura in the frontal area and pipetting out the fluid. The cerebrospinal fluid is diluted with 100 ul of 0.9% NaCl solution, centrifuged in a microfuge for one minute, and the supernatant containing free drug is separated from the pellet containing liposomes before storage at 20° C. The brain in the cranial cavity is lifted out with a spatula and the cranial cavity is washed out thoroughly with a 0.9% NaCl solution to collect all drug remaining in the cranial compartment. The spinal cord is extruded forward into the cranial vault by inserting in the rostral direction a 19 gauge hypodermic needle in the low lumbar spinal canal at a point 2.5 cm rostral to the origin of the tail and then pushing 0.9% NaCl solution into the canal at high pressure. The empty spinal canal is then washed thoroughly with 0.9% NaCl solution to collect all the drug in the spinal canal. The brain compartment specimen is collected separately from the spinal specimens. The specimens are homogenized on ice with distilled water using a Dounce manual tissue grinder, sonicated to disrupt intact liposomes and filtered through the ultrafiltration membrane (YMT membrane). The ultrafiltrates are analyzed with HPLC.

The amount of the drug is measured in cranial and spinal compartments and in cerebral fluid.

In all cases, the liposomal steroid remained in the cranial or spinal compartments for as long as 24 days while the free drug almost completely disappears within the first 2.8 hours. In the cerebrospinal fluid the free drug appears immediately in the high concentration and is quickly eliminated from the cerebrospinal fluid within the 2.8 hours. The liposomal cortisone, on the other hand remains in the cerebrospinal fluid for as long as 16 days.

EXAMPLE IX

Intraarticular Injection of Nonconventional Liposome Steroidal Composition

This example illustrates the use of the nonconventional steroidal liposomes for treatment of arthritis, rheumatoid arthritis, tendonitis and other inflammatory diseases of the joints by injection of liposomal steroid into joints.

New Zealand rabbits of 2.5 to 3.5 kg are shaved around the joints of both hind legs. Between 8 and 9 a.m. the right joints received an intra-articular injection of 0.5 ml of freshly prepared nonconventional liposomes with encapsulated hydrocortisone (3 mg) the left joints are injected with 0.5 ml physiological saline as control. Blood samples are collected from the ear veins at timed intervals. The rabbits are kept in metabolism cages. The rabbits are anesthetized 24 or 48 hours after the i.a. injection and the joints rinsed with 2 ml of physiological saline ("synovial fluid"). Then they receive ml of Disulphine Blue TM 6.2 per cent s.c., between the toes of both hind paws to stain the lymph nodes. At death total synovectomy of both joints is carried out, the heads of the femur, fibula and tibia and the popliteal lymph nodes excised. The tissues were grouped as follows: (1) menisci, tendons, ligaments and cartilage scraped off from femur, fibula, tibia, patella and fabellas were put together and named as "menisci etc.", (2) "synovium", (3) "patella and fabellas", (4) "femur, fibula and tibia-heads", (5) "bone marrow" which was scraped out from femur, fibula and tibia, (6) popliteal "lymph nodes". Menisci etc., synovium and bone marrow are digested with Packard Soluene 350, the bones with concentrated $HClO_4/H_2O_2$(1:2 v/v). Aliquots of whole blood, plasma, synovial fluid and after centrifugation and the digested materials are subjected to liquid scintillation counting. In the fresh synovia the number of cells is counted and cell differentiation is carried out. Urine and faeces are collected daily aliquots of urine are subjected to liquid scintillation counting directly, aliquots of faeces after digest with Packard Soluene 350.

Nonconventional preparations give indistinguishably low plasma levels of radiolabel for 48 hour post i.a. injection. The levels range from 0.001 to 0.3 per cent of the dose in the whole rabbit blood.

The liposomes have shown the long term 150 hours retention of radiolabel in synovial fluid and therefore in the whole joint.

EXAMPLE X

Treatment of Arthritis by Intraarticular Administration of Steroid in Nonconventional Liposomes This example illustrates the effect of nonconventional liposome steroidal formulation in treatment of arthritis.

Experimental Arthritis

Male and female Old English rabbits (1.8-2.4 kg) are used. Before induction of the arthritis, hair is removed from both knee joints by the use of a commercial depilatory cream. A bilateral arthritis is induced by the intraarticular injection of a preformed insoluble complex of poly-D-lysine and hyaluronic acid into both knee joints (Shaw et al., 1979).

An acute inflammatory flare, superimposed on an underlying chronic arthritis, is induced by giving a second injection of the polylysine-hyaluronate complex 28 days after the first injection.

Measurement of Inflammation

Radiometric measurement of joint temperature was carried out with a Heimann KT41 radiation thermometer (Phillips and Phage Thomas, 1979). The radiation from an area of skin 0.6 cm in diameter situated on the anterolateral side of the knee over the joint space is measured. The diameter of the knee is measured in the coronal plane of the articular space with a calibrated spring-loaded Baty micrometer.

Treatment of Experimental Arthritis

Liposomes (0.5 ml) containing the cortisol (3 mg) encapsulated in nonconventional liposomes prepared according to Example III and conventional liposomes prepared according to Example I, are injected into one knee joint 4 days after the induction of the arthritis. The temperatures and diameters of injected and contralateral joints is monitored for 3–5 days after treatment. In the treatment of an acute inflammatory "flare" superimposed on a chronic arthritis, liposomes are injected 4 days after induction of the acute episode.

The effect of treatment of an experimental arthritis in rabbits with nonconventional liposomes containing cortisol is investigated after the arthritis had developed for 4 days. It had previously been demonstrated that maximum anti-inflammatory activity was observed when liposomes were injected at this time, decreased activity was observed when treatment was started at 8 and 15 days after induction.

Antiinflammatory activity of steroid encapsulated in nonconventional liposome showed a significant and sustained reduction in both joint temperature and diameter when compared to steroid encapsulated in conventional liposomes.

EXAMPLE XI

Intravenous Administration of Nonconventional Liposome Steroid Composition

This example illustrates the use of the nonconventional steroid liposomes for intravenous treatment of various diseases requiring steroidal treatment.

The nonconventional steroidal liposome composition prepared according to Example III was administered intravenously and the ability of mouse organs to bind and/or take up the radiolabel was studied. Liposome formulation was concentrated, if necessary, by adding one volume of 50% (w/v) sucrose in phosphate-buffered saline to 3 volumes of liposome suspension, centrifuging at 12 800×g for 10 minutes removing the concentrated upper liposome layer and diluting to required volume with phosphate-buffered saline.

All experiments were carried out using groups of male ICR mice weighing approximately 25 grams (the weight of any individual mouse was not more than 10% different from the group mean weight). Doses of nonconventional liposomes containing beclomethosome dipropionate spiked according to Example III were administered to a mouse via a tail vein. At the end of the experimental period mice were lightly anesthesized with diethyl ether and a 1 ml blood sample was rapidly removed from the jugular vein with a heparinized syringe. Livers and spleens were subsequently removed, weighed and set aside for analysis together with the remaining carcass. An attempt was made to remove and discard the bladder and its content from each carcass prior to storage. Three types of studies were performed as follows.

Three groups of three experimental mice were each given 0.2 ml phosphate-buffered saline containing free radioactive spike beclomethasone intravenously via a tail vein. Mice receiving imperfect injections were discarded. Groups of three mice were killed at 1, 5 and 24 hours after injection and their organs sampled as described above in order to determine the clearance of free beclomethasone.

All organ and carcass samples were stored at −20° prior to analysis. Aliquots of liver (approximately 0.2 grams), spleen (whole organ), whole blood (approximately 0.8 ml) and of the dose (0.05 ml) were transferred to pre-weighed combustion cups, re-weighed and then allowed to air-dry. The remaining carcass was placed in a container together with 75 ml of water and homogenized using a Williams polytron wet milling device (Brunwell Scientific, Rochester, N.Y.). Samples of the resulting slurry (approximately 1.5 grams) were weighed into combustion cups and allowed to air-dry for at least 24 hours. Dried samples were analyzed for total $^{14}C$ radioactivity by scintillation counting following combustion in a Packard Sample Oxidizer. Combustions were carried out in series, with the inclusion of appropriate blanks. A duplicate sample from every third animal was analyzed to monitor the combustion reproducibility. Values of sample cpm were corrected for variations in quench by use of a quench curve and averaged over the three experimental animals in a group. Total radioactivity in liver, spleen, carcass and 1.0 ml blood was calculated and converted to percent of encapsulated dose. When calculating carcass values an allowance for blood volume remaining after sampling was made, assuming the total blood volume of a mouse equals 7.3% body weight. Total radioactivity in vivo was estimated by summing values for liver, spleen, total blood volume and carcass.

Plasma concentration of free and encapsulated beclomethasone in nonconventional liposomes was determined. The results are shown in FIG. 7. Free beclomethasone disappears rapidly from the plasma, while the beclomethasone encapsulated in nonconventional liposomes remains circulating in the plasma as liposome plasma reservoir from which the amount of steroid is slowly released to the circulation.

EXAMPLE XII

Intraperitoneal Administration of Nonconventional Liposome Steroid Composition This example illustrates the use of nonconventional steroid liposomes for intraperitoneal treatment of internal inflammatory diseases.

Male Sprague-Dawley rats weighing 250–300 grams are used. Each rat is given an oral dose of soybean oil (4.0) mL/kg) and 1 hour later anesthetized with an injection of urethane (1.2 g/kg sc). A polyethylene cannula (PE 10, Clay Adams) is inserted into the thoracic duct proximal to the juglosubclavian junction according to the method of Saldeen and Linder, *Acta. Path.*, 49:433(1960). Another cannula (PE-50) is put into the left femoral artery, and a third is used to cannulate the urinary bladder. The anesthesia is maintained for the duration of the study. The rat is placed on a plate and kept at 37° C. in a supine position. Fluid balance is maintained with a 4 mL/h/kg infusion of saline containing 2.5 U/mL of herparin via the arterial cannula. The test liposome steroid formulation according to Example III or free drug suspension (5 mM in phosphate-buffered saline, 2 mL/kg) is administered intraperitoneally 30 minutes after surgery. Lymph and urine are collected continuously. Blood is sampled periodically over the 5-h study period. At the end of the study, rats are sacrificed and the peritoneal cavity is rinsed with at least 60 mL of saline and 20 mL of 1% Triton X-100 to recover unabsorbed liposomes and marker. Several lymph nodes in the portal, and superior mesenteric) and those around the thymus (left and right mediastinal, and parathymic) are excised for assay. The molecular weight cut-off of the peritoneal-vascular permeability barrier is determined using sucrose, inulin, and fluorescein isothiocyanate (FITC) dextrans of molecular weights 20,000, 70,000, and 150,000; these are dosed intraperitoneally as phosphate-buffered saline solutions (sucrose and inulin at 5 mM; FITC dextrans at 20 mg/mL with 2 mL/kg injected). Steroid incorporated in this nonconventional liposome was retained in the peritoneal cavity for significantly longer periods than free drug.

EXAMPLE XIII

Topical Application of Nonconventional Liposome Steroidal Composition

This example illustrates the use of the nonconventional steroidal liposomes for topical treatments.

The effect of topical application of the steroid fluocinolone, both encapsulating in liposomes and as a free drug dissolved in acetone, has been evaluated using the female hamster flank organ as a model system.

The nonconventional steroid liposome radiolabeled composition according to Example III was used.

The hamster flank organ test was carried out according to the method described in Endocrinology. 92:1216–1222 (1983).

The female hamsters are separated into six groups of five animals and treated according to the following scheme.

Group I: 4 ug fluocinolone (dissolved in acetone);
Group II: 20 ug of free fluocinolone (dissolved in acetone);
Group III: 40 ug fluocinolone (dissolved in acetone);
Group IV: 4 ug fluocinolone (encapsulated in nonconventional liposomes);
Group V: 20 ug fluocinolone (encapsulated in nonconventional liposomes);
Group VI: 40 ug fluocinolone (encapsulated in liposomes);
Group VII: 40 ug fluocinolone (encapsulated in liposomes).

The animals are treated once daily (five days a week). After 28 days of treatment the flank organs are excised for morphometrical and histochemical examination according to the method of Goos et al., *Arch. Derm. Res.* 273:333–341 (1982). Systemic absorption of free fluocinolone was significant from the acetone solution, but negligible from the liposome system.

What is claimed is:

1. A liposome consisting essentially of nonphospholipid lipid components and a steroidal drug.

2. The composition of claim 1 wherein the lipid component is a mixture of cholesterol and cholesterol salt.

3. The composition of claim 2 wherein the cholesterol salt is selected from the group consisting of sulfate, phosphate, stalate and maleate.

4. The composition of claim 3 wherein the cholesterol salt is cholesterol sulfate.

5. The composition of claim 4 wherein the ratio of cholesterol sulfate to cholesterol to a drug is from 30 to 70 mole % of cholesterol sulfate; from 20 to 50 mole % of cholesterol and from 0.1 to 20 mole % of the steroidal drug.

6. The composition of claim 5 wherein the ratio is 50:40:10.

7. The composition of claim 5 wherein the ratio is 55:40:5.

8. The composition of claim 6 wherein the steroidal drug is selected from the group consisting of aldosterone, beclomethasone, betamethasone, cholesterol, cloprednol, cortisone, cortivazol, estrogen, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone, testosterone and triamcinolone, or their respective pharmaceutically acceptable salts or esters.

9. The composition of claim 8 wherein the steroidal drug is beclomethasone.

10. The composition of claim 8 wherein the steroidal drug is cortisone.

11. The composition of claim 8 wherein the steroidal drug is hydrocortisone.

12. A method of treating allergic diseases by administering, by route other than by inhalation, to a person in need of such treatment a therapeutically effective amount of nonconventional liposome composition comprising nonphospholipid lipid components and a steroidal drug.

13. The method of claim 12 wherein the composition comprises 30 to 70 mole % of cholesterol sulfate, 20 to 50 mole % of cholesterol and from 0.1 to 20 mole % of a steroidal drug.

14. The method of claim 13 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamcinolone, testosterosone or their respective pharmaceutically acceptable salts or esters.

15. The method of claim 14, wherein the composition is 50 mole % of cholesterol sulfate, 40 mole % of cholesterol and 5 mole % steroid of claim 14.

16. The method of claim 14, wherein the composition is 50 mole % of cholesterol sulfate, 40 mole % of cholesterol and 10 mole % of steroid of claim 14.

17. A method of treating inflammatory diseases by administering, by route other than by inhalation, to a person in need of such treatment a therapeutically effective amount of nonconventional liposome composition comprising nonphospholipid lip components and a steroidal drug.

18. The method of claim 17 wherein the composition comprises 30 to 70 mole % of cholesterol sulfate, 20 to 50 mole % of cholesterol and from 0.1 to 20 mole % of a steroidal drug.

19. The method of claim 18 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamcinolone, testosterosone or their respective pharmaceutically acceptable salts or esters.

20. The method of claim 19, wherein the composition is 50 mole % of cholesterol sulfate, 40 mole % of cholesterol and 5 mole % steroid of claim 19.

21. The method of claim 19, wherein the composition is 50 mole % of cholesterol sulfate, 40 mole % of cholesterol and 10 mole % of steroid of claim 19.

22. A method of treating skin diseases by administering to the person in need of such treatment a therapeutically effective amount of nonconventional liposome composition comprising of a nonphospholipid lipid component and a steroidal drug.

23. The method of claim 22 wherein the composition comprises 30 to 70 mole % of cholesterol sulfate, 20 to 50 mole % of cholesterol and from 0.1 to 20 mole % of a steroidal drug.

24. The method of claim 23 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamicinolone, testosterosone or their respective pharmaceutically acceptable salts or esters.

25. The method of claim 24, wherein the composition is 50 mole % of cholesterol sulfate, 40 mole % of cholesterol and 5 mole % steroid of claim 24.

26. The method of claim 24, wherein the composition is 50 mole % of cholesterol sulfate, 40 mole % of cholesterol and 10 mole % of steroid of claim 24.

27. A method of treating arthritic diseases by administering to the person in need of such treatment a therapeutically effective amount of nonphospholipid liposome composition comprising nonphospholipid lipid components and a steroidal drug.

28. The method of claim 27 wherein the composition comprises 30 to 70 mole % of cholesterol sulfate, 20 to 50 mole % of cholesterol and from 0.1 to 20 mole % of a steroidal drug.

29. The method of claim 28 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamicinolone, testosterosone or their respective pharmaceutically acceptable salts or esters.

30. The method of claim 29, wherein the composition is 50 mole % of cholesterol sulfate, 40 mole % of cholesterol and 5 mole % steroid of claim 29.

31. The method of claim 29, wherein the composition is 50 mole % of cholesterol sulfate, 40 mole % of cholesterol and 10 mole % of steroid of claim 29.

32. A method of treating rheumatic diseases by administering to the person in need of such treatment a therapeutically effective amount of liposome composition, consisting essentially of nonphospholipid lipid and a steroidal drug.

33. The method of claim 32 wherein the composition comprises 30 to 70 mole % of cholesterol sulfate, 20 to 50 mole % of cholesterol and from 0.1 to 20 mole % of a steroidal drug.

34. The method of claim 33 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamicinolone, testosterosone or their respective pharmaceutically acceptable salts or esters.

35. The method of claim 34, wherein the composition is 50 mole % of cholesterol sulfate, 40 mole % of cholesterol and 5 mole % steroid of claim 34.

36. The method of claim 34, wherein the composition is 50 mole % of cholesterol sulfate, 40 mole % of cholesterol and 10 mole % of steroid of claim 34.

37. A process of preparing a nonconventional liposome steroidal composition comprising:
   a) mixing a cholesterol sulfate, cholesterol and a steroid drug in an appropriate ratio;
   b) dissolving the mixture a solvent;
   c) lyophilizing the mixture;
   d) resuspending the lyophilate in buffer;
   e) preparing the nonconventional liposomes; and
   f) optionally sizing the nonconventional liposomes by extrusion through a filter.

38. The process of claim 22 wherein the ratio of cholesterol sulfate to cholesterol to steroidal drug is from 30 to 70 mole % of cholesterol sulfate; from 20 to 50 mole % of cholesterol and from 0.1 to 20 mole % of the steroidal drug.

39. The method of claim 33 wherein the drug is selected from the group consisting of aldosterone, beclomethasone, betamethasone, cholesterol, cloprednol, cortisone, cortivazol, deoxycortone, desonide, dexamethasone, difluorocortolone, estrogen, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamicinolone, testosterosone or their respective pharmaceutically acceptable salts or esters.

40. The process of claim 39 wherein the ratio of cholesterol sulfate to cholesterol to drug is 50:40:10 mole %.

41. The process of claim 37 wherein the liposomes are prepared by sonication.

42. The process of claim 37 wherein the liposomes are prepared by thin film hydration.

43. The process of claim 37 wherein the liposomes are prepared by solvent injection.

* * * * *